(12) United States Patent
Armand et al.

(10) Patent No.: US 10,710,964 B2
(45) Date of Patent: Jul. 14, 2020

(54) ORGANIC ELECTROLYTE COMPOUNDS FOR REDOX-FLOW BATTERIES

(71) Applicant: FUNDACIÓN CENTRO DE INVESTIGACIÓN COOPERATIVA DE ENERGÍAS ALTERNATIVAS CIC ENERGIGUNE FUNDAZIOA, Miñano, Álava (ES)

(72) Inventors: Michel Armand, Paris (FR); Javier Carretero-Gonzalez, Alava (ES); Elizabeth Castillo Martinez, Alava (ES); Estibaliz Coya, Alava (ES)

(73) Assignee: FUNDACION CENTRO DE INVESTIFACION COOPERATIVA DE ENERGIAS ALTERNATIVAS CIC ENERGIGUNE FUNDAZIOA, Minano, Alava (ES)

( * ) Notice: Subject to any disclaimer, the term of this patent is extended or adjusted under 35 U.S.C. 154(b) by 214 days.

(21) Appl. No.: 15/563,757

(22) PCT Filed: Mar. 31, 2016

(86) PCT No.: PCT/EP2016/056997
§ 371 (c)(1),
(2) Date: Oct. 3, 2017

(87) PCT Pub. No.: WO2016/156451
PCT Pub. Date: Oct. 6, 2016

(65) Prior Publication Data
US 2018/0079721 A1     Mar. 22, 2018

(30) Foreign Application Priority Data

Apr. 1, 2015 (EP) .................................. 15382163

(51) Int. Cl.
*H01M 8/00* (2016.01)
*C07D 209/36* (2006.01)
(Continued)

(52) U.S. Cl.
CPC ............ *C07D 209/36* (2013.01); *H01M 8/00* (2013.01); *H01M 8/1016* (2013.01); *H01M 8/188* (2013.01); *H01M 2300/0025* (2013.01)

(58) Field of Classification Search
CPC .. C07D 209/36; H01M 8/188; H01M 8/1016; H01M 8/00; H01M 2300/0025
(Continued)

(56) References Cited

U.S. PATENT DOCUMENTS

2011/0143223 A1   6/2011   Tokita et al.
2014/0024102 A1   1/2014   Sakai et al.
(Continued)

FOREIGN PATENT DOCUMENTS

WO    2015032480 A1    3/2015

OTHER PUBLICATIONS

International Search Report and Written Opinion dated Jun. 14, 2016 for PCT/EP2016/056997.
(Continued)

*Primary Examiner* — Gary D Harris
(74) *Attorney, Agent, or Firm* — Lucas & Mercanti, LLP

(57) ABSTRACT

The present invention relates to redox electrolyte compounds. The present invention further relates to a redox-flow battery wherein one of the catholyte and the anolyte, or both, has the redox electrolyte compound of the invention. The present invention further relates to the method of controlling the redox-flow battery and its use for energy storage.

13 Claims, 11 Drawing Sheets

(51) Int. Cl.
*H01M 8/1016* (2016.01)
*H01M 8/18* (2006.01)

(58) Field of Classification Search
USPC .......................................................... 429/72
See application file for complete search history.

(56) References Cited

U.S. PATENT DOCUMENTS

2014/0370403 A1* 12/2014 Narayan ............... H01M 8/188
429/418
2016/0116430 A1 4/2016 Nauber et al.

OTHER PUBLICATIONS

C. Cachet-Vivier, et al; Electrochemistry of powder material studied by means of the cavity . . . ; Electrochimica Acta; vol. 47; 2001; pp. 181-189.
M. Duduta, et al; Semi-solid lithium rechargeable flow battery; Materials Views; Adv. Energy Materials; vol. 1; 2011; pp. 511-516.
P. Fanjul-Bolado, et al; Electrochemical characterization of screen-printed and conventional carbon paste . . . ; Science Direct; Electrochimica Acta; vol. 53; 2008; pp. 3635-3642.
B. Huskinson, et al; A metal-free organic-inorganic aqueous flow battery; Letter; Nature; vol. 505; 2014; pp. 195-198 (16 pages).
K. Inoue, et al; Purification and characterization of OmcZ, an outer-surface, octaheme c-type cytochrome essential . . . ; Applied and Environmental Microbiology; vol. 76; No. 12; 2010; pp. 3999-4007.
B. Li, et al; Ambipolar zinc-polyiodide electrolyte for a high-energy density aqueous redox flow battery; Nature Communications; 2015; 8 pages.
R. Lin, et al; Microelectrode study of pore size, ion size, and solvent effects on the charge/discharge behavior of . . . ; Journal of the Electrochemical Society; vol. 156; No. 1; 2009; pp. A7-A12.
Y. Lu, et al; Rechargeable alkali-ion cathode-flow battery; Journal of Materials Chemistry; vol. 21; 2011; pp. 10113-10117.
M. Skyllas-Kazacos, et al; Progress in flow battery research and development; Journal of the Electrochemical Society; vol. 158; No. 8; 2011; pp. R55-R79.
B. Yang, et al; An inexpensive aqueous flow battery for large-scale electrical energy storage based on . . . ; Journal of the Electrochemical Society; vol. 161; No. 9; 2014; pp. A1371-A1380.

* cited by examiner

Fig. 3(a)
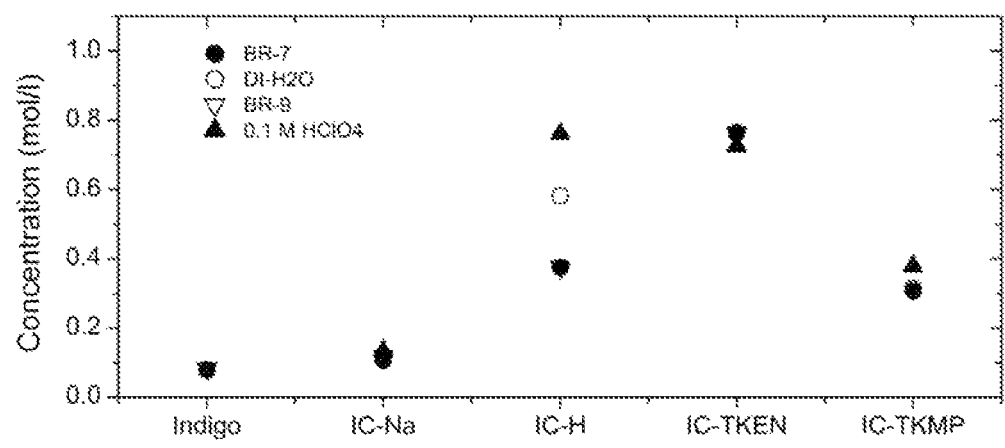
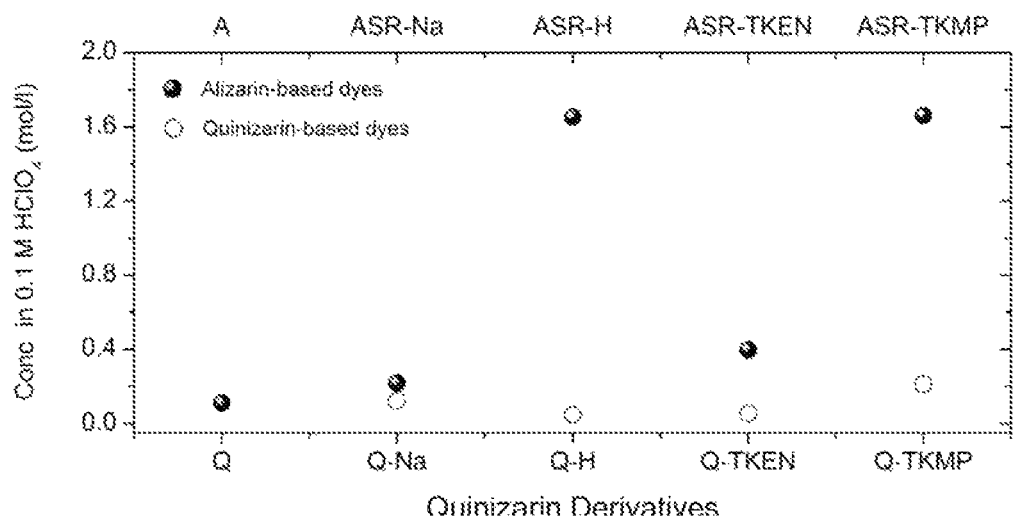
Fig. 3(b)

Fig. 4(a)
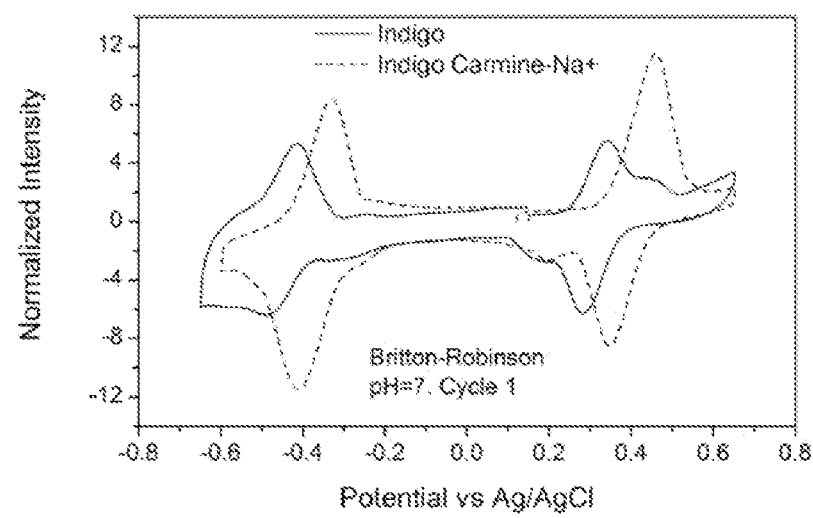
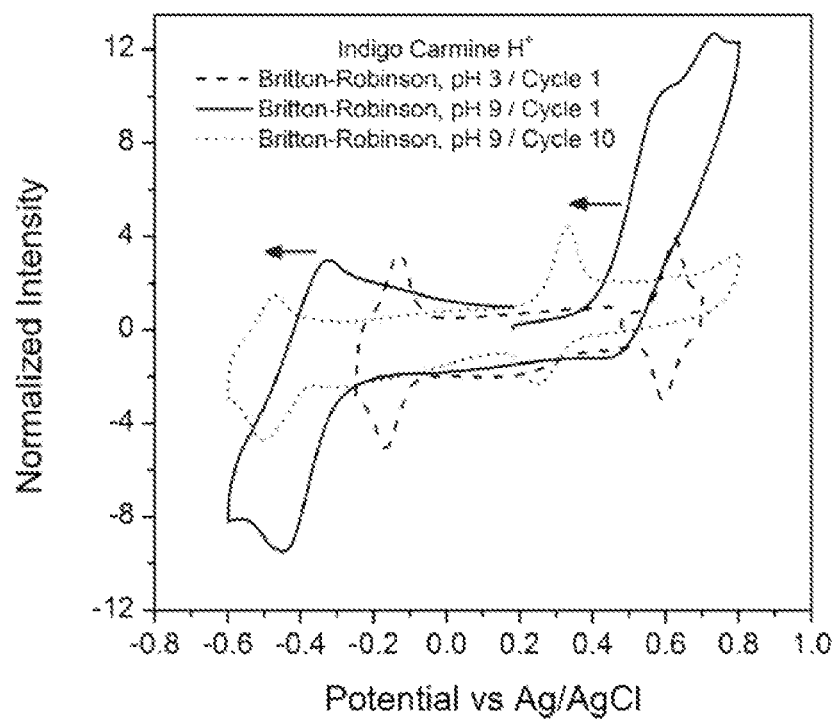
Fig. 4(b)

Fig. 4(c)
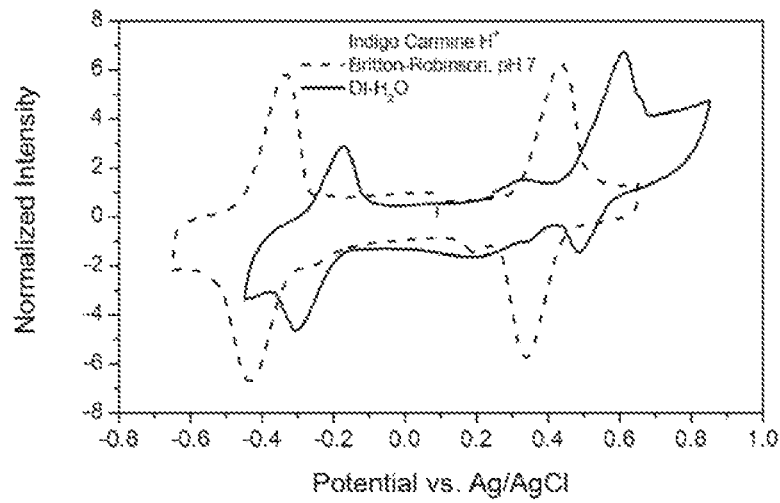
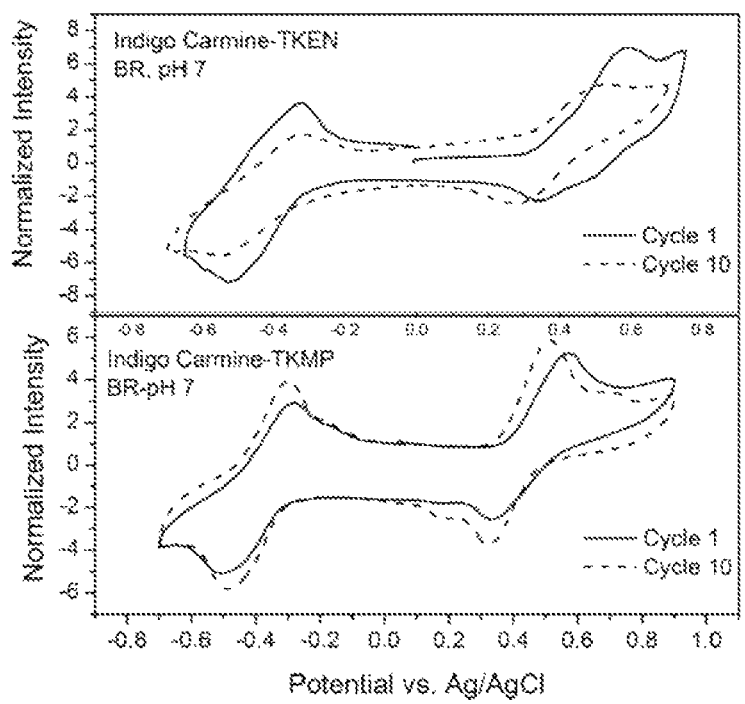
Fig. 4(d)

ORGANIC ELECTROLYTE COMPOUNDS FOR REDOX-FLOW BATTERIES

CROSS REFERENCE TO RELATED APPLICATION

This Application is a 371 of PCT/EP2016/056997 filed on Mar. 31, 2016, which, in turn, claimed the priority of European Patent Application No. 15382163.2 filed on Apr. 1, 2015, both applications are incorporated herein by reference.

FIELD OF THE INVENTION

The present invention is comprised in the field of organic electrolytes compounds, and, more particularly, to the field of organic electrolytes compounds suitable for redox-flow batteries.

BACKGROUND

Concerns over the environmental consequences of burning fossil fuels have led to an increasing use of renewable energy generated from sources such as solar and wind. However, the intermittent nature of such renewable energy sources has made it difficult to fully integrate these energy sources into electrical power grids and distribution networks. A solution to this problem has been to employ large-scale electrical energy storage (EES) systems, which are widely considered to be an effective approach to improve the reliability, power quality, and economy of renewable energy derived from solar or wind sources. Among the most promising large-scale EES technologies are redox-flow batteries. Redox-flow batteries are special electrochemical systems that can repeatedly store and convert megawatt-hours (MWhs) of electrical energy to chemical energy and chemical energy back to electrical energy when needed.

A common electrochemical cell configuration in redox-flow batteries includes a positive electrode and a negative electrode in separated tanks and separated by an ion-exchange membrane, and two circulating electrolyte solutions, positive and negative electrolyte flow streams, generally referred to as the "catholyte" and "anolyte", respectively. The energy conversion between electrical energy and chemical potential occurs instantly at the electrodes once the electrolyte solutions begin to flow through the cell. Redox-flow batteries can be recharged by inversing the flow of the redox fluids and applying current to the electrochemical reactor. Common redox-flow batteries are those based on redox systems comprising $Fe^{3+}/Fe^{2+}$ salts as anolyte and $Cr^{2+}/Cr^{3+}$ as catholyte. However, the ion-selective membranes separating the electrodes are not totally impermeable to chromium cations, and after some operation time, the chromium species diffuse in the iron compartment and vice-versa, decreasing the life-time of the redox-flow battery.

Even so, redox-flow batteries are the preferred large-scale EES technology since their capacity (energy) and their current (power) can be easily dissociated, and therefore easily scaled up. This is, energy can be increased by increasing the number or size of the tanks whereas the power is controlled by controlling the number and size of the current collectors rather than by changing the size of the electrolyte reservoirs. However both approaches imply using heavy and enormous tanks among other issues such as big pumps. Therefore, extensive research is being developed to optimize energy and power of the redox-flow batteries by using the right chemistry that maximizes the solubility of the redox couples in the electrolyte solution. The improvement of the solubility is crucial because of the enhancement of the mass transport of the reduced and oxidized ionic species leads to charge and discharge in the flow battery at higher current densities (power), and because higher concentration of redox ions leads to higher energy density of the cell. Vanadium-based redox chemistry, widely used in redox-flow batteries, exhibits solubilities of around 2 mol/l (1.26 V; 25-40 Wh/Kg). Although 8 mol/l of zinc iodide can be dissolved in zinc-polyiodide electrolyte-based systems, these are not totally redox-flow type as the deposition of solid zinc imposes a large electrochemical reactor [B. Li et al., Nature Communications 6, 6303 (2015)]. Similar limitations apply to zinc bromine systems (1.2 V; 80 Wh/Kg) [M. Skyllas-Kazacos et al., J. Electrochem. Soc. 158 (8) R55-R79 (2011)].

Li-ion based-chemistry has been also proved to increase energy density in redox-flow batteries, for example, using high-density slurries containing high- and low-voltage high capacity lithium ion intercalation compounds as catholyte and anolyte, respectively in an organic solvent [M. Duduta et al., Adv. Energy Mater. 1, 511-516 (2011)]. High viscosities and safety issues regarding the use of flammable organic solvents in the liquid electrolyte are salient disadvantages of the above systems. Alternatively using aqueous-based electrolytes containing alkali redox active ions in the catholyte side separated by an ion-conducting solid (ceramic) electrolyte from metallic alkali metal (i.e. Li or Na) have been proposed [Y. Lu et al., J. Mater. Chem. 21, 10113 (2011)]. However, the low conductivity of lithium ion through the ceramic electrolyte needs to be improved. Hence, aqueous-based redox-flow batteries, such as Vanadium (VRB) are still the most widespread chemistry in redox-flow batteries. However, some of the electroactive materials used in these aqueous redox-flow batteries are expensive, difficult to recycle, scarce and toxic (i.e. noble metals like Vanadium and the presence of highly aggressive chemicals like concentrated sulfuric acid).

Carbonylic compounds having acceptor (i.e. keto-carbonyl) or donor (i.e. enol/alcohol, amine-N—H, thiol) groups connected by a conjugated carbon-carbon skeleton that enables the delocalization of the n-electrons during the redox reactions have been also proposed as an alternative. These organic redox pairs undergo reversible and multiple proton-coupled electron transfer reactions having rate constants at least one order of magnitude higher than that of vanadium ions. However, two different organic molecules need to be used in order to have the acceptor and the donor functionalities at the same time [B. Yang et al., J. Electrochem. Soc. 161, (9) A1371-A1380, (2014)]. In addition, these compounds exhibit limited solubility in water [P. Fanjul-Bolado et al., Electrochim. Acta 53, 3635-3642, 2008]. This low solubility in water can be overcome by incorporating a sulphonic or hydroxyl functional group to the organic frame by simple chemical reactions. The presence of chemical substituents also allows tuning the standard reduction potential of the organic molecule and possibly enlarging the energy density of the flow cell. Recently, Aziz and co-workers [B. Huskinson et al., Nature, 505, 195-198 (2014)] have shown high-energy storage efficiency in a metal-free aqueous based flow battery by using low-cost quinone-disulphonic acid derivatives, more specifically an oxidized 9,10-anthraquinone-2,6-disulphonic acid as anolyte in a hybrid organic-inorganic cell. However, the use of bromine as oxidizer in this system is a hazard issue due to toxicity and corrosion. Anthraquinone-2,6-disulphonic acid and 1,2-benzoquinone-3,5-disulphonic acid as anolyte and catholyte, respectively, has been also published recently in a full organic cell [B. Yang et al., J. Electrochem. Soc. 161, 9, A1371-A1380, 2014]. In both documents, a two proton-coupled-electron transfer reaction was evidenced for a maximum solubility up to 1 M for the quinone molecules in acid media. In addition, and as for inorganic couples, there is not a full rejection rate of the membrane for both organic moieties, so the anolyte and catholyte will ultimately diffuse into each other, diminishing accordingly the energy density, thus increasing the size of the tanks needed.

The use of anthraquinone derivatives is also disclosed in WO2015/032480, particularly the compound anthraquinone-2-sulfonate, as a component of liquid electrolytes for electrochemical gas sensors for detection of $NH_3$ or $NH_3$-containing gas mixtures. Said anthraquinone derivative, as well as indigo polysulfonates, have also been used as redox mediators in aqueous redox electrolytes to ensure a good equilibrium between the redox centers and the working electrode in microbial fuel cells (Kengo Inoue et al., Appl. Env. Microbiol., 2010, 76(12), 3999-4007).

In view of above, there is a need for the development of low-cost and non-toxic redox electrolyte compounds with high water-solubility, fast kinetics and involving reversible and multiple proton-coupled electron-transfer redox reactions that could be used as integrality the anolyte or/and the catholyte, and thus reducing, the membrane leakage, in order to meet the market necessities.

BRIEF DESCRIPTION OF THE INVENTION

The present invention has been developed in view of the problems and needs of the state of the art described above. Therefore, an object of the present invention is to provide metal-free redox electrolyte compounds with high water-solubility and electrochemical activity.

The authors of the present invention have found that vat dyes-based compounds having acceptor and donor functionalities in the same molecule are highly water-soluble compounds exhibiting three-redox states. They are also environmentally friendly, less expensive and easy to commercialize than currently used redox electrolytes since they are derivatives of commercial vat-dyes.

These vat dyes-based compounds are also characterized for having a particular substitution pattern which, as pointed out in the experimental part of this specification, provides said compounds with better electrochemical performance than other dyes-based compounds having different substitutions in the molecule.

Therefore, a first aspect of the present invention relates to a redox organic electrolyte comprising a compound selected from:

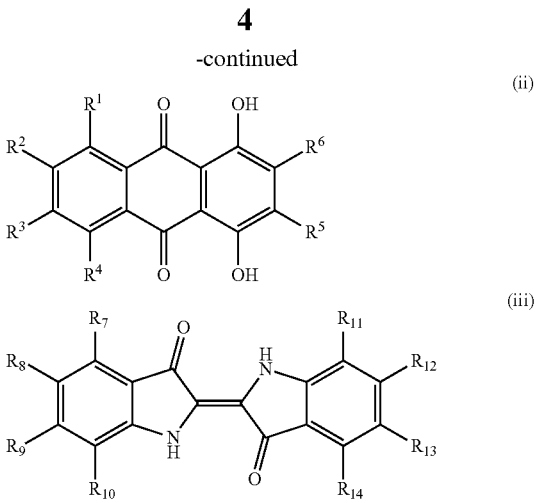

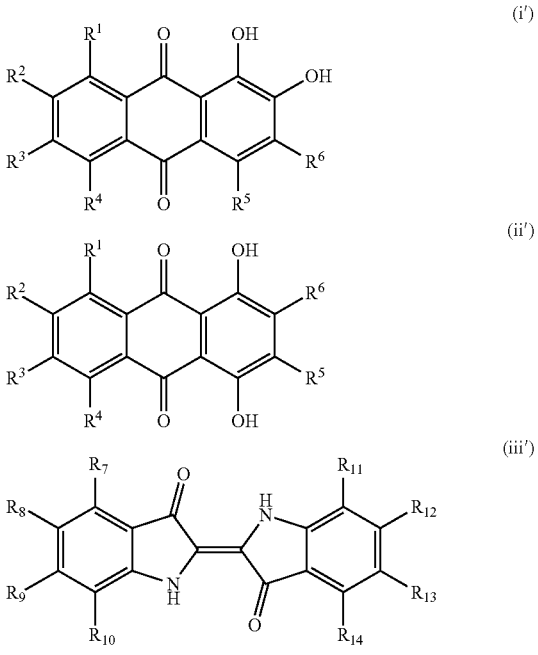

salts and isomers thereof;
wherein:
$R_1$-$R_6$ are independently selected from hydrogen; $C_1$-$C_6$ alkyl, optionally substituted with at least one halogen and/or optionally having at least one of O- and N-atom in the alkyl chain; $CO_2H$; OH; $NR^{15}R^{16}$ and $SO_3^-M^+$;
provided that at least one of $R_1$-$R_6$ is $SO_3^-M^+$;
$R_7$-$R_{14}$ are independently selected from hydrogen; $C_1$-$C_6$ alkyl, optionally substituted with at least one halogen and/or optionally having at least one of O- and N-atom in the alkyl chain; $CO_2H$; OH; $NR^{15}R^{16}$ and $SO_3^-M^+$;
provided that two of $R_7$-$R_{14}$ are $SO_3^-M^+$;
and wherein:
$R^{15}$ and $R^{16}$ are independently selected from H and $C_1$-$C_6$ alkyl; and $M^+$ is a cation selected from $H^+$, $Li^+$, $Na^{30}$, ½ $Mg^{++}$, ½ $Ca^{++}$, ammonium cation, phosphonium cation, imidazolium cation and mixtures thereof.

In a second aspect, the present invention refers to a compound selected from:

salts and isomers thereof;

wherein:

$R_1$-$R_6$ are independently selected from hydrogen; $C_1$-$C_6$ alkyl, optionally substituted with at least one halogen and/or optionally having at least one of O- and N-atom in the alkyl chain; $CO_2H$; OH; $NR^{15}R^{16}$ and $SO_3^-M^+$;
provided that at least one of $R_1$-$R_6$ is $SO_3^-M^+$;

$R_7$-$R_{14}$ are independently selected from hydrogen; $C_1$-$C_6$ alkyl, optionally substituted with at least one halogen and/or optionally having at least one of O- and N-atom in the alkyl chain; $CO_2H$; OH; $NR^{15}R^{16}$ and $SO_3^-M^+$; provided that two of $R_7$-$R_{14}$ are $SO_3^-M^+$;

and wherein:

$R^{15}$ and $R^{16}$ are independently selected from H and $C_1$-$C_6$ alkyl; and $M^+$ is a cation selected from an ammonium cation, a phosphonium cation and an imidazolium cation.

A further aspect of the present invention relates to a redox-flow battery comprising a cathode cell comprising a cathode and a catholyte; an anode cell comprising an anode and an anolyte; and an ion exchange membrane disposed between the cathode cell and the anode cell, wherein one of the catholyte or the anolyte comprises the redox organic electrolyte as defined above.

The compounds comprised in the redox electrolyte of the present invention contains both donor and acceptor groups in the same conjugated organic skeleton, allowing to use the same electrolyte as anolyte and catolyte in the redox-flow battery, lowering the price of the system and thus, the energy cost. In addition, some of the said compounds allow using non-acidic conditions for operation, enabling less corrosive media than currently achieved for example with vanadium-based systems.

Therefore, in a further aspect, the present invention relates to a redox-flow battery comprising a cathode cell comprising a cathode and a catholyte; an anode cell comprising an anode and an anolyte; and optionally an ion exchange membrane disposed between the cathode cell and the anode, wherein both the catholyte and the anolyte comprise the same redox organic electrolyte as defined above.

Moreover, another aspect of the present invention relates to the use of the previously defined redox-flow battery in energy storage.

Finally, another aspect of the present invention relates to the use of a redox organic electrolyte as defined above for the preparation of redox-flow supercapacitors, electrochromic displays and photochemical cells.

BRIEF DESCRIPTION OF THE DRAWINGS

FIG. 3. Solubility of the redox-active salts. Maximum concentration of each carbonyl-containing organic dye in different aqueous media at room temperature. (a) Indigo and (b) bis-quinones derivatives.

DETAILED DESCRIPTION OF THE INVENTION

Figure 1:
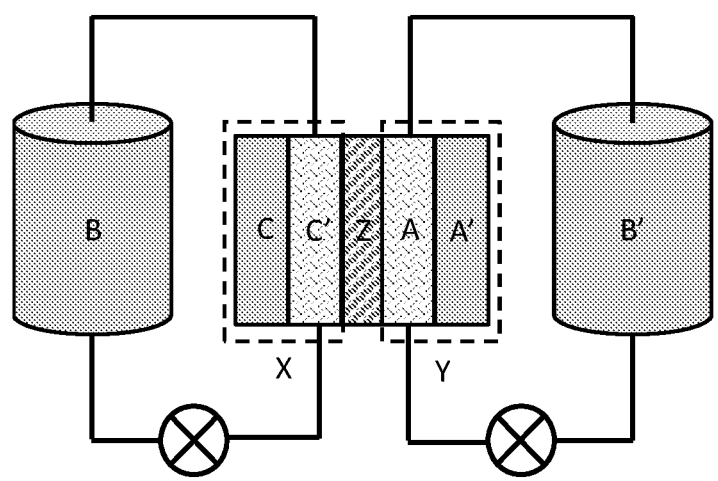
FIG. 1. Scheme of the single component redox-flow battery of the invention.

Unless defined otherwise, all technical and scientific terms used herein have the same meaning as commonly understood to one of ordinary skill in the art to which this disclosure belongs.

Redox Organic Electrolyte

The present invention relates to a redox organic electrolyte comprising a compound selected from:

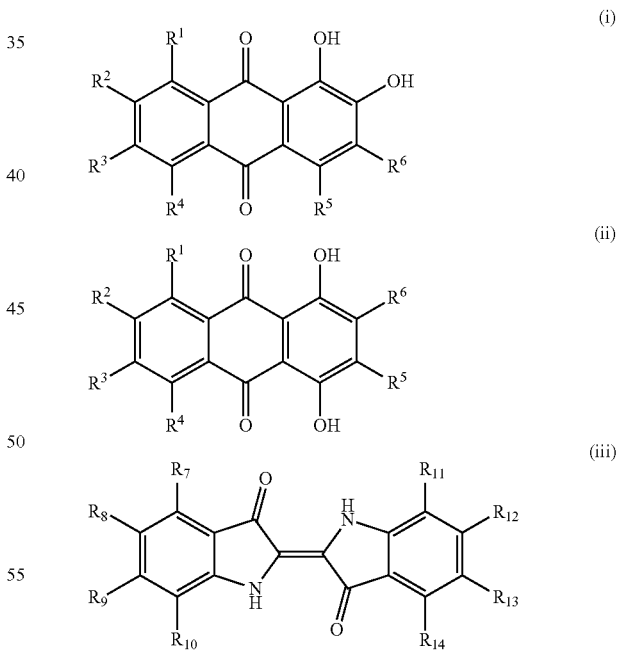

salts and isomers thereof;

wherein $R_1$-$R_6$ are independently selected from hydrogen; $C_1$-$C_6$ alkyl, optionally substituted with at least one halogen and/or optionally having at least one of O- and N-atom in the alkyl chain; $CO_2H$; OH; $NR^{15}R^{16}$ and $SO_3^-M^+$; provided that at least one of $R_1$-$R_6$ is $SO_3^-M^+$;

$R_7$-$R_{14}$ are independently selected from hydrogen; $C_1$-$C_6$ alkyl, optionally substituted with at least one halogen and/or optionally having at least one of O- and N-atom in the alkyl chain; $CO_2H$; OH; $NR^{15}R^{16}$ and $SO_3^-M^+$;
provided that two of $R_7$-$R_{14}$ are $SO_3^-M^+$;
and wherein:

$R^{15}$ and $R^{16}$ are independently selected from H and $C_1$-$C_6$ alkyl; and $M^+$ is a cation selected from $H^+$, $Li^+$, $Na^+$, $\frac{1}{2}Mg^{++}$, $\frac{1}{2}Ca^{++}$, ammonium cation, phosphonium cation, imidazolium cation and mixtures thereof.

In the context of the present invention, the term "salt" is to be understood as any form of the redox electrolyte compound as defined above in an ionic form or charged and coupled to a counter-ion (a cation or anion). No limiting examples of suitable salts are salts of alkali metals, of alkaline earth metals, ammonium salts or phosphonium salts.

In the context of the present invention, the term "isomer" as used herein includes constitutional isomers and zwitterionic isomers.

Constitutional isomers refer to as tautomers. Specifically, the term "tautomer" refers to one of two or more structural isomers of a compound that exist in equilibrium and are readily converted from one isomeric form to another. In the particular case of the compounds (i) and (ii) used in the invention, the keto-enol tautomeric pair (equilibrium between the keto- and enol-forms) may be present. The interconversion to constitutional isomers (tautomers) occurs by intramolecular acid-base chemical reactions with the migration of a proton and the adjustment of a single bond and adjacent double bond.

Furthermore, compounds used in the invention may exist as zwitterionic isomers. In the particular case of the compounds of formula (iii) used in the invention, the corresponding zwitterion molecules may be present, which are electrically neutral, containing positive and negative charges localized on nitrogen and oxygen atoms, respectively.

In the context of the present invention, the term "$C_1$-$C_6$ alkyl" refers to a monovalent group derived from a straight or branched chain saturated aliphatic hydrocarbon, and having between 1 and 6 carbon atoms. Alkyl groups include, for example, methyl, ethyl, propyl, isopropyl, and hexyl.

In the context of the present invention, "at least one halogen" refers to a group wherein at least one hydrogen atom of an alkyl group has been replaced by fluorine, chlorine, bromine, or iodine.

In the context of the present invention, "at least O— or N— atom in the alkyl chain" refers to a N or O atom intercalated in the alkyl chain, i.e., located between two carbon atoms of an alkyl group.

The organic compounds of formula (i)-(iii) are vat dyes derivatives. Vat dyes are a class of dyes that are classified as such because of the method by which they are applied. Vat dyeing is a process that refers to dyeing that takes place in a bucket or vat. Most common vat dyes are derivatives of Indigo dye and of anthraquinones (for example, halogenated or methylated derivatives).

The compounds of formula (i) and (ii) are derivatives of anthraquinone. Anthraquinone dyes (also called anthracenedione or dioxoanthracene) are dyes formed by an aromatic organic compound with formula $C_{14}H_8O_2$. Several isomers are possible, each of which can be viewed as a quinone derivative. The term anthraquinone, however, almost invariably refers to one specific isomer, 9,10-anthraquinone wherein the keto groups are located on the central ring. Synthetic dyes are often derived from this isomer 9,10-anthraquinone, such as Alizarin (1,2-dihydroxy-9,10-anthraquinone) and Quinizarin (1,4-dihydroxy-9,10-anthraquinone).

Particularly, the compound of formula (i) is a derivative of Alizarin, and therefore, it is characterized for having two hydroxyl groups at positions 1 and 2 of the molecule, in addition to have at least one substituent —$SO_3^-M^+$ group at any other position.

The compound of formula (ii) is a derivative of Quinizarin, and therefore, it is characterized for having two hydroxyl groups at positions 1 and 4 of the molecule, in addition to have at least one substituent —$SO_3^-M^+$ group at any other position.

The particular pattern substitution in compounds (i) and (ii) has been shown to impair a remarkably improvement in their electrochemical performance when compared to anthraquinone derivatives having hydroxyl substituents at other positions of the molecule.

Indigo dyes are dyes formed by an organic compound, 2,2'-Bis(2,3-dihydro-3-oxoindolylidene) with a distinctive blue color (Indigo), historically, extracted from plants, but nearly all indigo dyes produced today are synthetic.

Particularly, the compound of formula (iii) is a derivative of Indigo having two sulfonate groups.

Indigo derivatives of formula (iii) having two sulfonate groups also provide an improved electrochemical performance when compared to indigo derivatives having more than two sulfonate substituents.

According to the experimental data provided below, and contrary to the results with other anthraquinone and indigo derivatives, the use of sulfonate anthraquinone derivatives having hydroxyl substituents at positions 1,2 and 1,4, as well as the use of disulfonate indigo derivatives, yields two symmetric redox peaks in the voltammetry measurements, thus giving rise to reversible redox reactions.

For compounds of formula (i)-(iii), the electron density donor (—OH or —NH—) and acceptor (C=O) groups linked by conjugated bonds in its molecular structure yield hybrid resonant species after external stimuli are applied (chromism). It has been evidenced in the present invention that by applying an electrochemical potential, the compounds of formula (i)-(iii) are able of both, reversibly oxidize and reduce, developing two-sets of fast two proton-electron transfer highly reversible redox peaks (Scheme 1). Both processes are separated by approximately 1 V, due to the optimal charge delocalization along the extensive conjugation in its molecular structure.

(i)

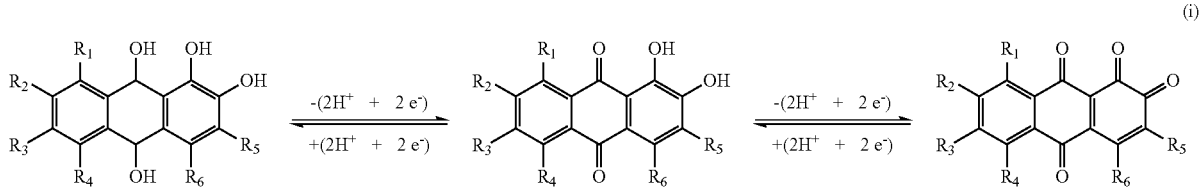

-continued

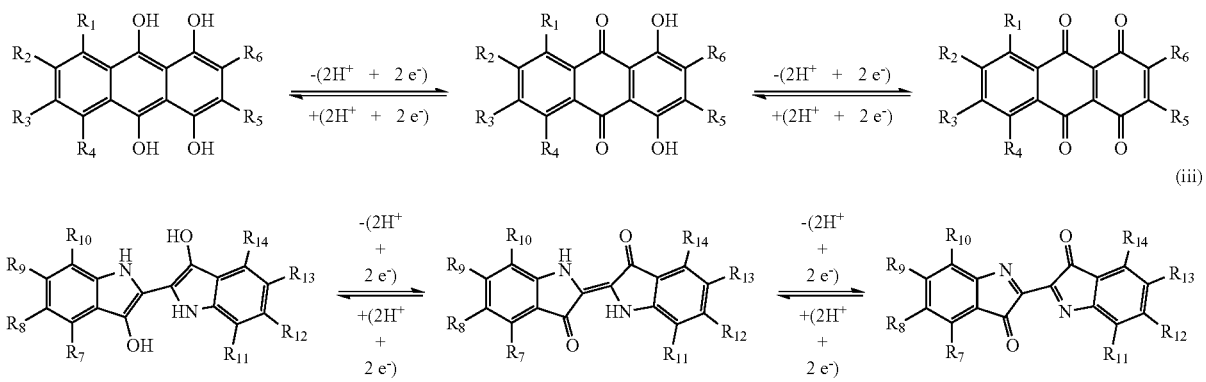

Scheme 1. Three-redox stages. Donor (—OH for compounds (i) and (ii) and —NH for compounds (iii)) and acceptor (—C═O) groups connected through conjugated bonds enable three-redox stages so that two reversible electrochemical reactions involving proton-electron transfers can be observed.

Therefore, the above described molecular frameworks are characterized by having three-redox states, so that the following two two-proton-electron coupled transfer reversible reactions in one single molecule are observed: ↔ ↔ wherein $QH_2$ represents any of the compounds of formula (i)-(iii) used in the invention.

Thus, at least two electrons are transferred in each redox process, which means that for the same solubility, the capacity of these compounds is doubled when compared to traditional electrolytes based on vanadium compounds. Furthermore, the voltage difference between oxidation and reduction is only 1 V instead of 1.4 V in systems based on vanadium compounds which means that the potential increase in energy density is about 40%.

In a particular embodiment, in the compound of formula (i) and (ii) $R_1$-$R_6$ are independently selected from hydrogen; $C_1$-$C_6$ alkyl, optionally substituted with at least one halogen and/or optionally having at least one of O- and N-atom in the alkyl chain; $CO_2H$; OH; and $SO_3^-M^+$, provided that at least one of $R_1$-$R_6$ is $SO_3^-M^+$.

In another particular, in the compound of formula (i), $R^1$-$R^5$ are all H, and $R^6$ is $SO_3^-M^+$, wherein $M^+$ is selected from $H^+$, $Li^+$, $Na^+$, an ammonium cation and a phosphonium cation.

More preferably, in this particular embodiment, $M^+$ is selected from $H^+$, $Li^+$, $Na^+$, $[N(CH_2CH_2OH)_4]^+$, $[CH_3N(CH_2CH_2OH)_3]^+$, $[(CH_3)_2N(CH_2CH_2OH)_2]^+$ and $[P(CH_2OH)_4]^+$. Even more preferably, $M^+$ is selected from $H^+$, $Li^+$, $Na^+$, $[N(CH_2CH_2OH)_4]^+$ and $[P(CH_2OH)_4]^+$.

In another particular embodiment, in the compound of formula (ii), $R^1$-$R^5$ are all H, and $R^6$ is $SO_3^-M^+$, wherein $M^+$ is selected from $H^+$, $Li^+$, $Na^+$, an ammonium cation and a phosphonium cation.

More preferably, in this particular embodiment, $M^+$ is selected from $H^+$, $Li^+$, $Na^+$, $[N(CH_2CH_2OH)_4]^+$, $[CH_3N(CH_2CH_2OH)_3]^+$, $[(CH_3)_2N(CH_2CH_2OH)_2]^+$ and $[P(CH_2OH)_4]^+$. Even more preferably, $M^+$ is selected from $H^+$, $Li^+$, $Na^+$, $[N(CH_2CH_2OH)_4]^+$ and $[P(CH_2OH)_4]^+$.

In another particular embodiment, in the compound of formula (iii), $R^9$ and $R^{12}$ are $SO_3^-M^+$. In a more preferred embodiment, $R^7$-$R^8$, $R^{10}$-$R^{11}$ and $R^{13}$-$R^{14}$ are all H, and $R^9$ and $R^{12}$ are $SO_3^-M^+$, wherein $M^+$ is independently selected from $H^+$, $Li^+$, $Na^+$, ½ $Mg^{++}$, an ammonium cation and a phosphonium cation.

More preferably, in this particular embodiment, $M^+$ is selected from $H^+$, $Li^+$, $Na^+$, ½ $Mg^{++}$, $[N(CH_2CH_2OH)_4]^+$, $[CH_3N(CH_2CH_2OH)_3]^+$, $[(CH_3)_2N(CH_2CH_2OH)_2]^+$ and $[P(CH_2OH)_4]^+$. Even more preferably, $M^+$ is selected from $H^+$, $Li^+$, $Na^+$, ½ $Mg^{++}$, $[N(CH_2CH_2OH)_4]^+$ and $[P(CH_2OH)_4]^+$.

In a preferred embodiment, the redox organic electrolyte comprises a compound selected from the group consisting of:

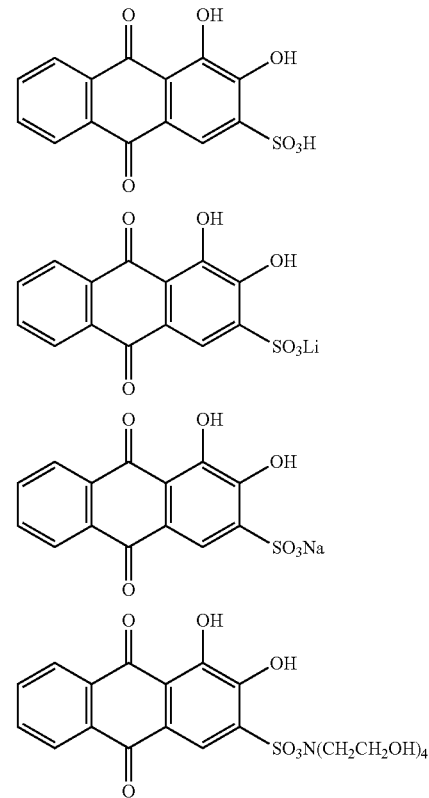

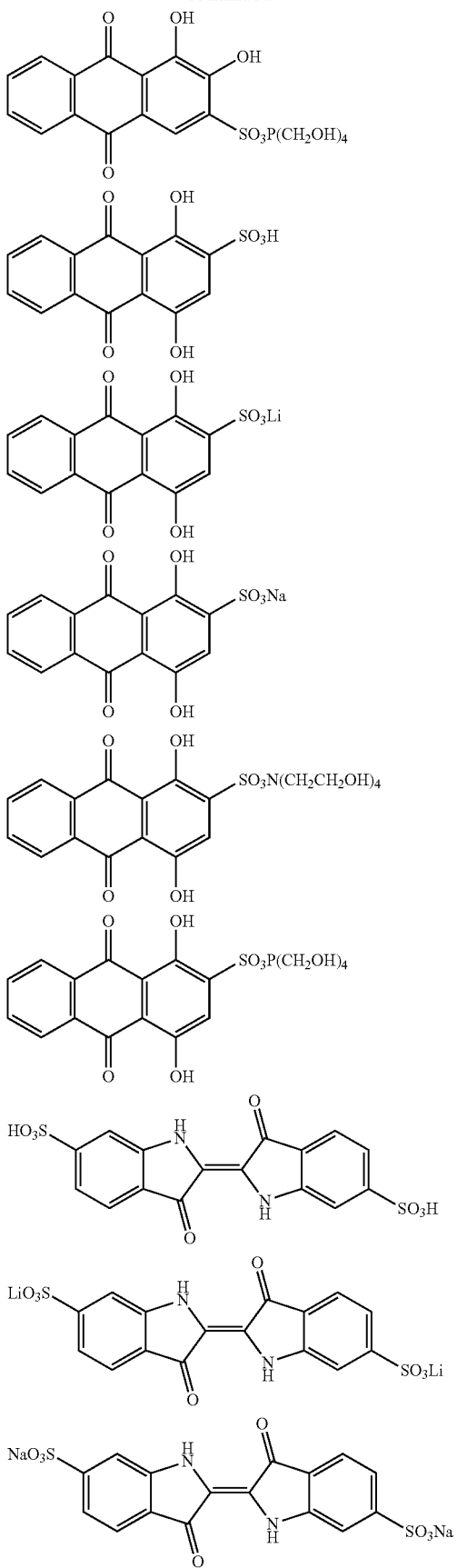

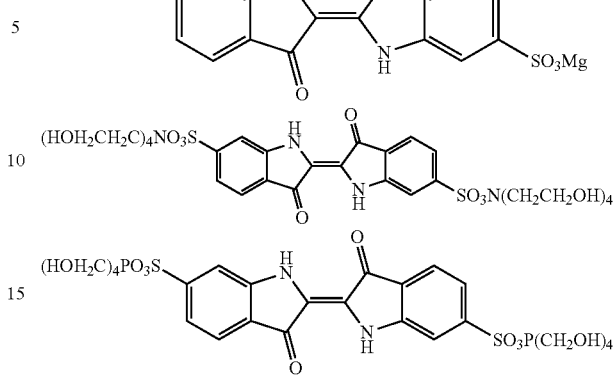

In a particular embodiment, the redox organic electrolyte of the present invention is in a liquid phase, either with or without a separate solvent.

In a preferred embodiment, the redox organic electrolyte of the present invention is in a liquid phase forming an electrolyte solution.

In the context of the present invention, the term "electrolyte solution" refers to a solution electrically conductive which comprises a solid electrolyte dissolved in a liquid medium.

Thus, in this particular embodiment, the redox organic electrolyte of the present invention comprises a compound selected from a compound (i), (ii) and (iii) as mentioned above and a solvent.

Examples of solvents may include an aqueous solvent, a non-aqueous solvent, or a mixture thereof. Examples of the aqueous solvent may include water, as well as aqueous solutions of a least one compound selected from $HClO_4$, $H_3BO_3$, $CH_3COOH$, $CH_3SO_3H$ $CF_3SO_3H$ $H_2SO_4$, $K_2SO_4$, $Na_2SO_4$, $H_3PO_4$, $H_4P_2O_7$, $K_2HPO_4$, $Na_3PO_4$, $K_3PO_4$, $HNO_3$, $KNO_3$, HCl, NaOH, KOH and $NaNO_3$ and mixtures thereof. Examples of non-aqueous solvents include acetonitrile, γ-butyrolactone ("GBL"), a cyclic carbonate (such as propylene carbonate ("PC"), ethylene carbonate ("EC"), and butylene carbonate), N-methyl-2-pyrrolidone ("NMP"), N,N-dimethylformamide ("DMF"), N,N-dimethylacetamide ("DMA"), dimethylsulfoxide ("DMSO"), dimethyl sulfone (DMS02), sulfolane, chlorobenzene, cyclopentanone, tetrahydrofuran, 1,4-dioxane, methanol, ethanol, ethylene glycol, diethylene glycol, triethylene glycol, tetraethylene glycol, their mono or dimethyl ethers, 1,2 propylene glycol, 1,3 propylene glycol and mixtures thereof.

In a preferred embodiment, the electrolyte solution as defined above comprises water as solvent.

In fact, the presence of at least one group $SO_3^-M^+$ in the compounds used in the electrolyte of the invention, and particularly the cation $M^+$, allows improving the water-solubility of said compounds. Therefore, in the organic compounds (i)-(ii), at least one of $R_1$-$R_6$ is a sulfonyl group $SO_3^-M^+$ wherein $M^+$ is a cation selected from $H^+$, $Li^+$, $Na^+$, $K^+$, ½ $Mg^{++}$, ½ $Ca^{++}$, ammonium cation phosphonium cation, imidazolium cation and mixtures thereof, whereas in the organic compounds (iii), at least two $R_7$-$R_{14}$ are a sulfonyl group $SO_3^-M^+$, wherein $M^+$ is a cation selected from $H^+$, $Li^+$, $Na^+$, $K^+$, ½ $Mg^{++}$, ½ $Ca^{++}$, ammonium cation phosphonium cation, imidazolium cation and mixtures thereof.

Said functional group $SO_3^-M^+$ can be incorporated in the dyes Alizarin, Quinizarin and Indigo to obtain compounds of formula (i)-(iii) by simple chemical reactions known by those skilled in the art, such as those described in the experimental part of this document.

By the optimal selection of the counter-cation $M^+$, the water-solubility of the compounds (i)-(iii) used in the electrolyte of the present invention can be further increased.

It has also been evidenced that the total solubility of the compounds of formula (i)-(iii) in water can be boosted further up to 1.5 M, while maintaining a reversible charge transfer and a large electrochemical potential window. The advantage of a highly-water soluble single component redox-flow cell is an increase in the energy density and reduction of storage tank sizes.

All these findings are of high significance because the same electrolyte could be used as catholyte and anolyte in a 1 V redox flow cell, while exhibiting very high solubility and chemical stability in water media, therefore promoting current energy storing technologies where the electrolyte and the electrode material are in liquid form such as, for example, in redox flow batteries.

In another particular embodiment, the redox organic electrolyte of the present invention comprises a compound selected from a compound (i), (ii) and (iii) as mentioned above in the molten state.

Another aspect of the present invention refers to some of the compounds of formula (i)-(iii). Particularly, the invention is also directed to a compound selected from:

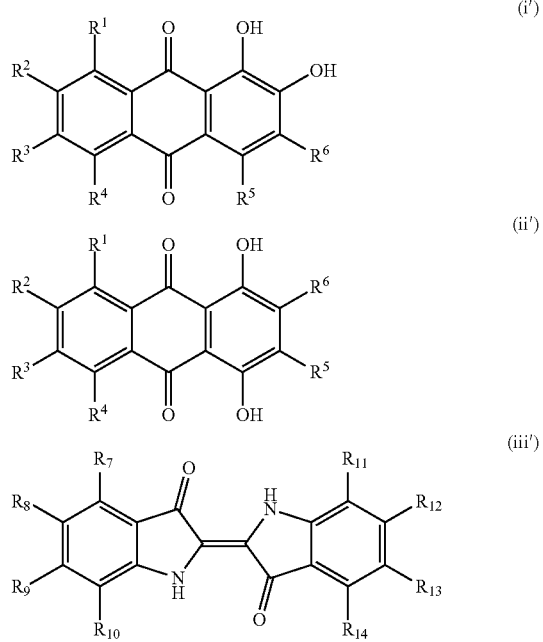

salts and isomers thereof;
wherein:
$R_1$-$R_6$ are independently selected from hydrogen; $C_1$-$C_6$ alkyl, optionally substituted with at least one halogen and/or optionally having at least one of O- and N-atom in the alkyl chain; $CO_2H$; OH; $NR^{15}R^{16}$ and $SO_3^-M^+$; provided that at least one of $R_1$-$R_6$ is $SO_3^-M^+$.

$R_7$-$R_{14}$ are independently selected from hydrogen; $C_1$-$C_6$ alkyl, optionally substituted with at least one halogen and/or optionally having at least one of O- and N-atom in the alkyl chain; $CO_2H$; OH; $NR^{15}R^{16}$ and $SO_3^-M^+$;
provided that two of $R_7$-$R_{14}$ are $SO_3^-M^+$;
and wherein:
$R^{15}$ and $R^{16}$ are independently selected from H and $C_1$-$C_6$ alkyl; and $M^+$ is a cation selected from ammonium cation, phosphonium cation, and an imidazolium cation.

It has been found that the exchange of the protons ($H^+$) that counterbalance the negative charge from the sulfonic group appended to the structure of the molecules by an organic cation $M^+$, which is non-chelatable and hygroscopic, such as that defined in the compounds of formula (i')-(iii') of the invention, leads to the creation of hydrosoluble salts that melts near ambient temperature.

In a particular embodiment, in the compound of formula (i') and (ii') $R_1$-$R_6$ are independently selected from hydrogen; $C_1$-$C_6$ alkyl, optionally substituted with at least one halogen and/or optionally having at least one of O- and N-atom in the alkyl chain; $CO_2H$; OH; and $SO_3^-M^+$; provided that at least one of $R_1$-$R_6$ In another particular, in the compound of formula (i'), $R^1$-$R^5$ are all H, and $R^6$ is $SO_3^-M^+$, wherein $M^+$ is a cation selected from an ammonium cation and a phosphonium cation, and an imidazolium cation.

In another particular embodiment, in the compound of formula (ii'), $R^1$-$R^5$ are all H, and $R^6$ is $SO_3^-M^+$, wherein $M^+$ is a cation selected from an ammonium cation, a phosphonium cation, and an imidazolium cation.

In another particular embodiment, in the compound of formula (iii'), $R^9$ and $R^{12}$ are $SO_3^-M^+$, even more preferably $R^7$-$R^8$, $R^{10}$-$R^{11}$ and $R^{13}$-$R^{14}$ are all H, and $R^9$ and $R^{12}$ are $SO_3^-M^+$, wherein $M^+$ is independently selected from an ammonium cation and a phosphonium cation.

In a particular embodiment, in the compounds of formula (i'), (ii') and (iii') as defined above, $M^+$ is selected from $[N(CH_2CH_2OH)_4]^+$, $[CH_3N(CH_2CH_2OH)_3]^+$, $[(CH_3)_2N(CH_2CH_2OH)_2]^+$ and $[P(CH_2OH)_4]^+$. Even more preferably, $M^+$ is selected from $[N(CH_2CH_2OH)_4]^+$ and $[P(CH_2OH)_4]^+$.

Redox-Flow Battery

Another aspect of the present invention relates to a redox-flow battery comprising a cathode cell comprising a cathode and a catholyte; an anode cell comprising an anode and an anolyte; and an ion exchange membrane disposed between the cathode cell and the anode, wherein one of the catholyte or the anolyte comprises the redox organic electrolyte as defined above.

In a particular embodiment, the redox-flow battery further comprises a catholyte tank and an anolyte tank wherein the catholyte tank and the anolyte tank is each respectively in fluid communication with the cathode cell and the anode cell.

FIG. 1 shows a diagram schematically illustrating a redox-flow battery according to the present invention. Referring to FIG. 1, the redox-flow battery includes a cathode cell (X) and an anode cell (Y), which are divided by an ion exchange membrane (Z). The cathode cell (X) and the anode cell (Y) respectively include a cathode (C) and a catholyte (C') and an anode (A) and an anolyte (A'). The cathode cell (X) is connected to a cathode tank (B) for providing and discharging the catholyte (C'). Similarly, the anode cell (Y) is connected to an anode tank (B') for supplying and discharging an anolyte (A'). The ion exchange membrane (Z) prevents ions of active materials of the catholyte (C') and the anolyte (A') from being mixed with each other.

The redox flow battery is discharged by connecting it to an external circuit having an electric load to make a current to flow out, and is charged by connecting it to an external power source to make a current to flow in.

As the ion exchange membrane, an ion exchange membrane that is used in typical redox flow battery may be used without any limitation. Non-limiting examples of cation exchange membranes include a cation exchange membrane obtained by sulfonating a styrene-divinylbenzene copolymer, a cation exchange membrane introducing a sulfonic acid or a carboxylic side group by using a copolymer of tetrafluoroethylene and perfluorosulfonylethoxyvinylether (Nafion® membrane from DuPont, Flemion® membranes from Asahi Glass) as a base, a cation exchange membrane formed of a copolymer of tetrafluoroethylene and a perfluoro vinylether having a carboxyl group at a side chain, or a cation exchange membrane introducing a sulfonic acid group by using an aromatic polyether sulfone copolymer as a base.

Non-limiting examples of anion exchange membrane include anion exchange membrane obtained by introducing a chloromethyl group to a styrene-divinylbenzene copolymer that is a base, followed by amination; an anion exchange membrane obtained by a formation of a quaternary pyridinium salt of a vinylpyridine-divinylbenzene copolymer, or an anion exchange membrane obtained by introducing a chloromethyl group to an aromatic polysulfone copolymer that is a base, followed by amination. Commercially available anion exchange membranes are NEO-SEPTA-AMEX, NEOSEPTA-AHA, NEOSEPTA-ACS, which are manufactured by Astom; Cybron ionan MA3475, which is manufactured by Lanxess; FAS, FAN, FAB, FAA, FAD, which are manufactured by FuMa-atech; and PC 100D, PC200D, PC-SA which are manufactured by Poly-merchemie Altmeier; Nafion® membrane from DuPont, Flemion® membranes from Asahi Glass, Dowex® membranes from Dow chemical; and Amberlite® from Rohm & Haas.

In the redox-flow battery of the present invention, the same redox organic electrolyte may be used as both the catholyte and the anolyte, making membrane leakage an unimportant issue. In fact, a membrane-less redox-flow battery may be designed using microfluidics. In addition, the ion-exchange membrane can be replaced by a microporous separator, like Celgard®, or from Tanen®.

Therefore, another aspect of the present invention relates to a redox-flow battery comprising a cathode cell comprising a cathode and a catholyte; and anode cell comprising an anode and an anolyte; and optionally an ion exchange membrane disposed between the cathode cell and the anode cell, wherein both the catholyte and the anolyte comprise the same redox electrolyte compound as defined above.

In this particular embodiment, the redox-flow battery may further comprise a catholyte tank and an anolyte tank respectively connected to the cathode cell and the anode cell to transfer the fluids.

Another particular embodiment refers to the redox-flow battery as defined above, wherein at least one of the catholyte and the anolyte further comprise a supporting electrolyte. Supporting electrolytes may optimize the interactions between the organic electrolyte molecules and the solvent molecules that break the intermolecular bonds maximizing solubility, while attaining a fast proton transport mechanism by tuning the pH. Examples of supporting electrolyte may be at least one selected from $LiBF_4$, $LiPF_6$, $LiSbF_6$, $LiAsF_6$, $LiClO_4$, $LiCF_3SO_3$, $Li(CF_3SO_2)_2N$ $LiC_4F_9SO_3$, $LiAlCl_4$, $LiN(C_xF_{2x+1}SO_2)(C_yF_{2y+1}SO_2)$ (wherein x and y are integers numbers in the range $0 \leq x,y \leq 4$), $NaBF_4$, $NaPF_6$, $Na_2SO_4$, $TEAPF_6$, $TBAPF_6$, $TEABF_4$, $TBABF_4$, mineral acids like sulphuric acid and perchloric acid, and bases like KOH, Britton-Robinson buffers, sodium acetate, imidazol and methanesulfonamide buffers.

In a preferred embodiment, the supporting electrolyte as defined above is in a concentration 0.1 and 1 M.

In a preferred embodiment, the redox-flow battery as defined above has an energy density between 10 and 60 Wh/kg.

In a preferred embodiment, the redox-flow battery as defined above has a current density between 10 and 20000 $A/m^2$.

Another aspect of the invention is the use of the redox-flow battery as defined above in energy storage.

The redox-flow battery of the invention may be suitable not only for energy storage of renewable energy but also in mobile phones, portable computers and electric vehicles.

Furthermore, the novel and environmentally friendly redox organic electrolyte of the invention comprising the compounds of formula (i), (ii) and (iii) can also be applied, not only to redox-flow batteries, but also to other electrochemical systems like redox-flow supercapacitors, electrochromic displays and photochemical cells (dye-sensitized solar cells and photogenerator cells).

EXAMPLES

Materials and Methods

Attenuated Total Reflectance-Fourier Transform InfraRed (ATR-FTIR) spectra were recorded on Vertex 70 spectrometer (Bruker) in the range of wavelength of 4000-400 $cm^{-1}$. Differential Scanning Calorimetry measurements (DSC) were carried out on a TA Instruments Q2000 model in a sealed Al pan at a heating rate of 5° C. $min^{-1}$ in the temperature range between −80° C. and 100° C. The cyclic voltammetry measurements were performed in a cavity micro-electrode (CME) with an electrochemical interface area around a fraction of $mm^2$ and ohmic drop coming from the bulk of the electrolyte that can be neglected, allowing the use of high scan rates [C. Cachet-Vivier et al.; Electrochim. Acta 47, 181-189 (2001)]. The samples were studied electrochemically by using a three-electrode configuration cell in $DI-H_2O$ and the different supporting electrolytes with a platinum wire as counter electrode and Ag/AgCl or Hg/HgO as reference electrode depending of the acidic or basic pH of the media respectively.

PREPARATION OF EXAMPLES 1-6

Example 1: Preparation of Sulphonated Acid Sodium Salt Derivates 2 g (8.4 mmol) of commercial Quinizarin (Sigma-Aldrich) was treated with sodium sulphite ($Na_2SO_3$, 5 g, 40 mmol), and copper oxide (CuO, 1 g, 12 mmol) under reflux with water for 24 hours according to the procedure disclosed in P. G. Marshall, J. Chem. Soc. 3206-3208 (1931). The solution was acidified with diluted sulphuric acid ($H_2SO_4$) and filtered while boiling. A small amount of NaCl was added to the filtered portion. After cooling, the sulphonated organic sodium salt was extracted by centrifugation (15 min, 10000 rpm) as a mixture of orange-red needles and plates. The solid sulphonated organic sodium salt was dried under vacuum at 70° C. for 48 hours. The resulting compound is 1,4-dihydroxy-9,10-dioxo-2-anthracenesulfonic acid sodium salt, also referred to as Quinizarin-$SO_3Na$.

Sulphonated acid sodium salt derivatives of Alizarin and Indigo, respectively named Alizarin S. Red-$SO_3Na$(3,4- dihydroxy-9,10-dioxo-2-anthracenesulfonic acid sodium salt) and Indigo Carmine or Indigo Carmine-SO$_3$Na (3,3'-dioxo-2,2'-bis-indolyden-5,5'-disulfonic acid disodium salt) were commercially purchased from Sigma Aldrich.

Example 2: Hydrogen Ion-Exchange of Sulphonated Acid Sodium Salt Derivates

The sulphonated organic sodium salts obtained in Example 1 were flushed three times through a column containing the resin Amberlyst® 15 hydrogen form (Sigma-Aldrich) to convert them into their protonic acid analogs. Amberlyst® resin was pre-conditioned by passing first a 250 ml of 0.1 M H$_2$SO$_4$ and secondly Deionized—H$_2$O (DI-H$_2$O) (~250 ml) until the pH of the solution from the outlet of the column was 7. After that, 100 ml of an aqueous solution containing ~1 gram of sodium salt was introduced into the column. The whole process (conditioning +DI washing+Na-salt passing) was repeated. Then, the solvent was removed under reduced pressure and the solid collected was dried under vacuum at 70° C. during 48 hours. The resulting compound is referred to as Quinizarin-SO$_3$H.

Sodium ions were removed also from sulphonated acid sodium salt derivatives of commercial Alizarin and Indigo following the same procedure as above, giving rise to compounds, Alizarin-SO$_3$H (also referred to as Alizarin S. Red-H$^+$) and Indigo-SO$_3$H (also referred to as Indigo Carmine-H$^+$), respectively.

Example 3: Synthesis of Tetrakis(hydroxyethyl) ammonium Bromide [N(CH$_2$CH$_2$OH)$^{4+}$,Br$^-$] (TKEN-Br)

Triethanolamine (1 g, 6.77 mmol) was mixed with 2-Bromo-ethanol (0.84 g, 6.77 mmol) in a 25 ml vial under stirring during 5 days at 50° C. by using a hot plate with a silicon bath. After that the magnetic stirrer was removed from the reaction vial and the vial was placed in an oven at 70° C. during 5 more days. While still hot the liquid product was cooled and then the ammonium bromide salt, N(CH$_2$CH$_2$OH)$^{4+}$,Br$^-$, solidified into a waxy-like white solid. The solid was stored in a fridge at 8° C. until used.

Example 4. Synthesis of Tetrakis(hydroxyethyl) Ammonium Hydroxide [N(CH$_2$CH$_2$OH)$^{4+}$,OH$^-$] (TKEN-OH) by Hydroxide Exchange Chemical exchange of bromine by hydroxide anions was performed by using a column exchange containing a strongly basic resin (Dowex-Chloride 1×8, Sigma-Aldrich). The basic resin was first activated with 250 ml of an aqueous solution of 0.1 M KOH followed by 250 ml of DI-H$_2$O. Then an aqueous solution containing 1.5 g of [N(CH$_2$CH$_2$OH)$^{4+}$,Br$^-$] (Example 3) was flushed three times through the column being activated each time before. After exchange, the solvent was removed by rotavaporation under reduced pressure and then the TKEN-OH salt dried at 70° C. under vacuum during 48 hours. The salt was stored in a refrigerator at 8° C. until used. Special care must be taken during the drying process of TKEN-OH because of the possibility of thermal decomposition at temperatures higher than 100° C. [Doumaux, JR. A. R., Barnes, R. K. Reactions of Hydroxide Tetrakis(2-hydroxyethyl)ammonium. Journal of Organic Chemistry 38, 3630-3632 (1971)].

Example 5. Synthesis of TKEN-Based Redox Salts by Acid-Base Reaction (Titration)

The preparation of highly water-soluble stoichiometric neutral salts containing the TKEN organic cation was carried out by simple titration reaction between the basic TKEN-OH salt (OH form) and the acid form (H form) of the sulphonated organic compounds (Quinizarin-SO$_3$H, Alizarin-SO$_3$H, and Indigo-SO$_3$H of Example 2). The pH evolution during the acid-based reaction synthesis was followed by a pH meter immersed in an aqueous solution 0.1 M of the cations (OH form) or anions (H form) while the counter ion solution was added drop-wise. The by-product of the reaction was water. The solvent was removed under reduced pressure and the solid salt dried under vacuum at 70° C. during 48 hours. After that, the solvent was removed by vacuum distillation and the TKEN based salts dried under vacuum at 70° C.

Thus, the resulting products are Quinizarin-SO$_3$-TKEN; Alizarin S. Red-TKEN and Indigo Carmine-TKEN.

Example 6. Synthesis of TKMP-Based Neutral Salts by Cationic Exchange

The synthesis of the TKMP analogues salts by using tetrakis(hydroxymethyl)phosphonium chloride salt was performed in the following steps: i) flushing 0.5 ml of an aqueous solution of commercial tetrakis(hydroxymethyl) phosphonium chloride (80% in H$_2$O, Sigma-Aldrich) through a column containing an acidic exchange resin Amberlyst® 15 hydrogen form (Sigma-Aldrich). A chemical exchange between the hydrogen ion in the resin and the phosphonium cations take place with subsequent formation of hydrochloric acid; ii) washing the resin passing 250 ml of DI-H$_2$O through the column until pH=7 is achieved; iii) 100 ml of an aqueous solution containing an excess of the sulphonic sodium salts of Example 1 (Quinizarin-SO$_3$Na, Alizarin-SO$_3$Na, and Indigo-SO$_3$Na) is flushed twice through the column to maximize the reaction extension as much as possible between the anchored phosphonium based cations and the organic anions.

Thus, the resulting products are Quinizarin-SO$_3$-TKMP; Alizarin S. Red-TKMP and Indigo Carmine-TKMP.

Example 7. Characterization Tests

Figure 2A:
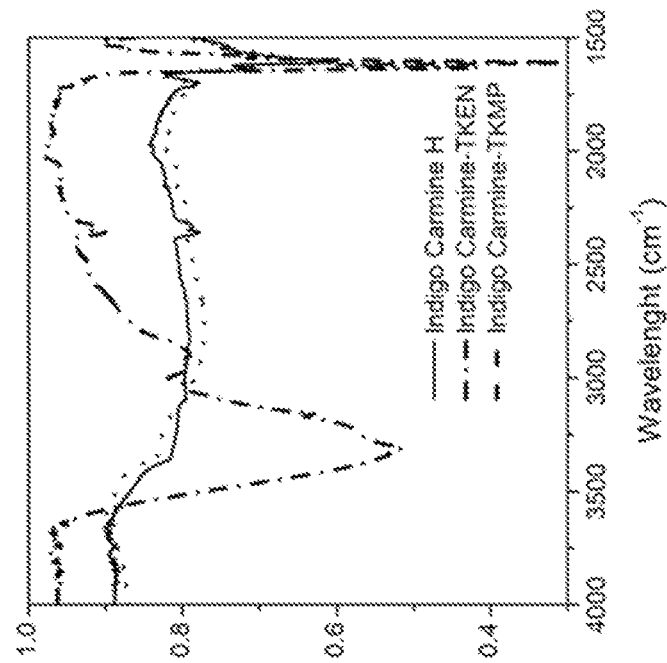
FIG. 2. Ion exchange. (a) acid-base titration curves obtained during the synthesis of the electrochemically active TKEN compounds; and (b)-(d) IR spectra of the Indigo, Alizarin and Quinizarin sulphonated salts with $H^+$ (solid line), $TKEN^+$ (dashed-dotted line) and $TKMP^+$ (dashed line) cations.
Figure 2B:
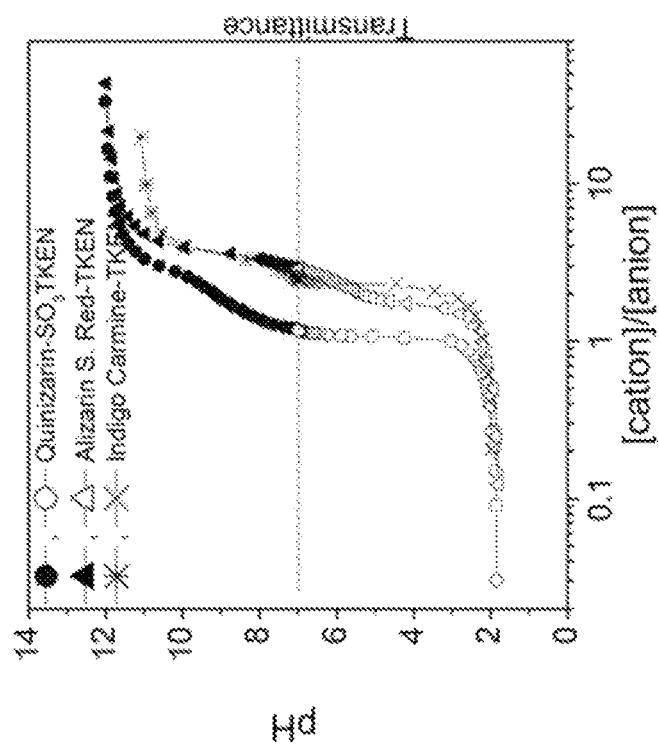
Figure 2C:
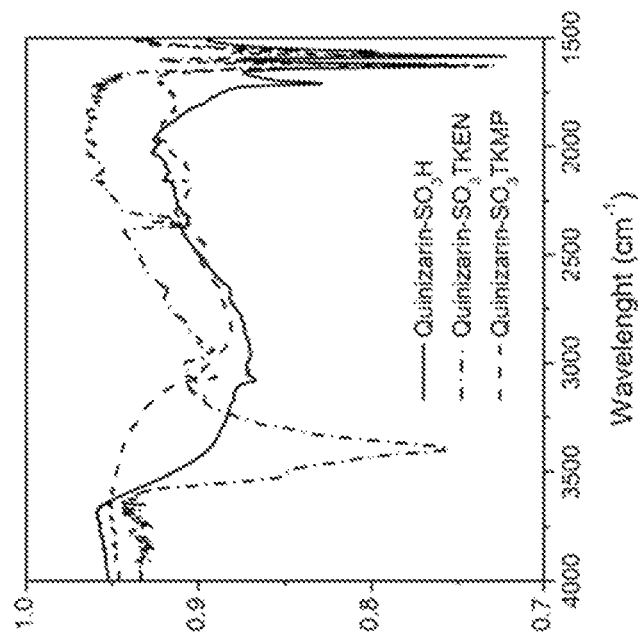
Figure 2D:
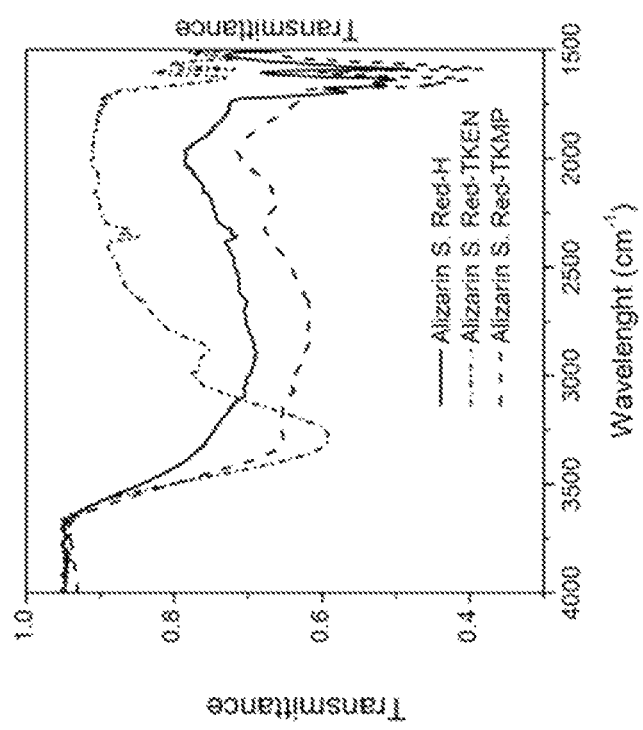

FIG. 2a shows pairs of acid-base titration curves corresponding to the synthesis of Quinizarin-SO$_3$-TKEN (Q-TKEN), Alizarin S. Red-TKEN (A-TKEN) and Indigo Carmine-TKEN (I-TKEN). Titration curves were performed either with a basic pH corresponding to a starting aqueous solution of the basic hydroxide ammonium salt (0.01-0.02 M) and then followed by dropping of an aqueous solution (0.01-0.02 M) of the protonated organic dye until pH 7 or vice-versa. Interestingly both methodologies gave the same [cation/anion] ratio at pH 7 for each salt, which is the pH at which the synthesis is considered as completed.

The corresponding characterization by Infrared spectroscopy of the protonated, TKEN and TKMP Indigo-SO$_3$—, Alizarin-SO$_3$— and Quinizarin-SO$_3$-derivatives is also shown in FIG. 2(b-d). A broad band ranging 3300-2000 cm$^{-1}$ corresponding to —OH vibration due to the presence of intermolecular hydrogen bonds as a consequence of the presence of water molecules (crystallization water) is clearly observed in the three-protonated compounds.

Moreover, an all-common weak band distinctly noticeable also corresponding to the —OH vibration of the water molecules at 1640-1615 cm$^{-1}$ is also evidenced. The IR spectra of the TKEN-containing salts (dashed-dotted curve) shows a sharp band ranging from approximately 3500 and 3100 cm$^{-1}$ corresponding to —OH vibration due to intramolecular bonds typically of alcohols. In addition, the disappearance of the weak but sharp band at 1640-1615 cm$^{-1}$ corresponding to —OH vibration due to crystallization of water molecules for the three TKEN-based salts is also clearly evidenced. In the case of the TKMP salts the vibration band corresponding to the intramolecular vibration of —OH moieties is less pronounced for A-TKMP and even negligible for Q-TKMP; however, a narrower vibration band (3200-2200 cm$^{-1}$), the disappearance of the relatively weak and sharp —OH vibration at 1640-1615 cm$^{-1}$ and the appearance of new weak and broader peaks for both A-TKMP and Q-TKMP salts, most probably corresponding to different intermolecular coordination (number and environment) of the water molecules is evidenced. For I-TKMP salt, (FIG. 2b) a broad band in the same range than for the bis-quinone counterparts (3200-2200 cm$^{-1}$) corresponding to vibration band of —OH from crystallization water molecules is observed. The weak and sharp —OH vibration at 1640 cm$^{-1}$ did not change the position but becomes a bit broader.

Example 8. Solubility Studies

These were conducted in glass vials of 25 ml volume in which the organic electrolyte compound mass ranging between 15-30 mg approximately was dissolved in DI-H$_2$O and also in the different supporting electrolytes. The procedure was performed in the following steps: after the addition of the solid, a small volume (usually starting from 25 μl) was added by using a micropipette, the suspension was vigorously shaken by hand until complete homogenization of the media in the whole vial (bottom part and walls) was observed. After that, the vials are left standing overnight. The day after, possible precipitation at the bottom of the vial was evaluated. If some solid appeared, the addition of more volume of solvent and/or supporting electrolyte was continued until the solid disappeared completely. Then, the vials were rotated-mixing overnight to make sure that complete solubility was achieved for a certain volume. The final concentration value was only calculated for those samples showing a stable solution after several weeks.

FIG. 3 show the solubility of the organic compounds accomplishing reversible redox activity, with the exception of Indigo Carmine-TKEN (I-TKEN) in DI-H$_2$O and Indigo series in 0.1 M HClO$_4$, which are included for comparison purpose. FIG. 3a shows the solubility properties of Indigo compounds in different aqueous based supporting electrolytes. A solubility enhancement is clearly evidenced by exchange of the counter ions of the sulphonated form. The highest concentration values of up to 0.76 M were obtained for I-TKEN dissolved in pure DI-H$_2$O and in aqueous BR buffer at pH=7 (BR-7), which means that high solubility can be achieved in a neutral medium. For comparison, solubility values in 0.1 M HClO$_4$ was also plotted in FIG. 3a. FIG. 3b shows the solubility results for the bis-quinone samples dissolved in 0.1 M HClO$_4$. High values about ~1.5 M were obtained for both Alizarin S. Red protonated (A-H) and the analogue exchanged with the tetrahydroxyl-phosphonium cation A-TKMP. However, different solubility was surprisingly obtained for Quinizarin derivatives compared to Alizarin derivatives (only differ in the —OH groups being in ortho vs. para positions). Moreover, in all the solutions containing that highly-water soluble neutral salts no precipitation were observed even after 6 months since their preparation.

Considering the two electron-proton process taking place in the present redox molecules, for a constant amount of grams of salt the optimization of the final concentration will be a balance between the molecular weight and the packing density of the organic compounds in the electrolyte solution. Highest concentration values and subsequently of chemical-electrical energy density stored in the present systems would be achieved as higher the packing density and lower the molecular weight of the molecule. The experimental density of the present solutions containing the redox neutral salts were measured. Densities of 1.04 g/ml, 1.00 g/ml and 0.95 g/ml were measured for solutions 1.23 M of Alizarine SH in H$_2$O, 1.17 M of Alizarine SH in H$_2$O and 1.46 M of Alizarine SH in 0.1 M HClO$_4$ respectively. The solubility values achieved are significant compared to the concentration of the standard-Vanadium batteries, which is ~1.5 M in Vanadium redox cells.

Example 9. Cyclic Voltammetry Measurements

The microcavity was filled with a homogenous mixture of active material (50 wt %) and carbon super C-65 (50 wt %) by applying pressure against an agate mortar. The cavity was cleaned by immersing the electrode in ethanol in an ultrasonic bath between experiments. For the CME, scan rates approximately an order of magnitude larger could be used without distortion usually seen in conventional cells [R. Lin et al., J. Electrochem. Soc. 1, A7-A12 (2009)]. All the experiments using CME were made three times for the same sample to check reliability. All the obtained results were found to be fully reproducible. Cyclic voltammetry experiments were done from 10 mV/s to 1 V/s using a multichannel potentiostat/galvanostat (VMP3, Biologic). In order to make a direct comparison between the different samples, all current values were normalized to current values measured in the pure capacitive behavior region. By doing this, the linear region of the entire electrode cyclic voltammogram were normalized to the same capacitance which should come from the 50% carbon and then comparable relative currents are obtained coming from faradaic reactions (proton-electron coupled transfer) of each organic compound in the different electrolytes.

Indigo Derivatives

FIG. 4 shows the CEM for Indigo family compounds measured in unbuffered DI-H$_2$O and aqueous BR buffer media at different pH. FIG. 4a shows two reduction peaks at positive (0.31 V) and at negative potential (−0.44 V) vs. Ag/AgCl ref. electrode for Indigo (continuous line) cycled in BR buffer at pH=7. Both pairs of peaks shifted anodically approximately 80 mV for Indigo Carmine-Na$^+$ (discontinuous line) as a consequence of the electron withdrawing character of the sulphonic groups. Interestingly, better charge efficiency was obtained for the sulphonated form. FIG. 4c shows the cyclic voltammograms for protonated Indigo Carmine-H$^+$ (I-H) in BR buffer at pH=7 (dashed-dotted line) and in neat DI-H$_2$O (continuous line). Both samples exhibited a peak separation of ~1 V, high redox reversibility and an open circuit voltage located symmetrically between the two redox peaks indicating an almost perfect electrochemistry for a redox salt that shows relatively high solubility values of ~0.4 M in BR buffer at pH=7 and ~0.6 M in neat DI-H$_2$O. The anodic shift of ~170 mV evidenced in DI-H$_2$O was mostly due to the slightly more acidic pH~6. Cyclic voltammetry studies shown in FIG. 4b confirmed the pH dependence for Indigo Carmine-H$^+$. The electrochemical cycling of I-H in BR buffer at pH=3 (discontinuous line) evidenced a pair of reversible reduction peaks separated by ~0.75 V while at pH=9 (continuous line) the wave at higher potential showed a quasi-reversible behavior during the first few cycles, then becoming more reversible as shifted to lower potential during cycling and stabilizing at cycle 10 with both peaks separated by ~0.8 V. The reason for such change in the wave potential could be the gradual basification of the nearby electrode interface as a consequence of the increase of dissolution of the acidic I-H salt while cycling. The peak current intensity for the I-H cycled at pH=3 and pH=9 is smaller than when it was cycled at neutral pH in aqueous BR buffered solution. FIG. 4d depicts the 1st and 10th cycle of the cyclic voltammetries for Indigo Carmine-TKEN (up) and Indigo Carmine-TKMP (bottom) recorded in an aqueous BR buffered solution at pH=7. Although peak intensity slightly decrease and there is a higher overpotential compared to the protonated I-H phase shown in FIG. 4c, the cyclic voltammogram for both novel redox salts consisted of two reversible set of redox peaks separated by 1 V. It is important to point out that concentration values up to 0.76 M were found for Indigo Carmine-TKEN and that with the addition of these good electrochemical properties makes these salts a highly desired material for being used as a low cost analyte in electrochemical systems working at neutral pH. Because of having 1V voltage difference between redox processes vs the 1.4 V of VRB, it would be possible to achieve the same energy density with Indigo Carmine-TKEN than with Vanadium redox species while using approximately twice less concentrated electrolyte solutions, of lower cost organic salts and using a less expensive membrane stable at neutral pH.

Furthermore, for comparative purposes, the cyclic voltammograms of indigo derivatives having three and four sulfonate substituents were also tested. The particular compounds were:

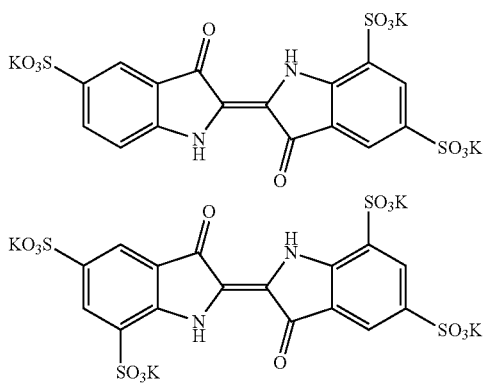

Figure 4E:
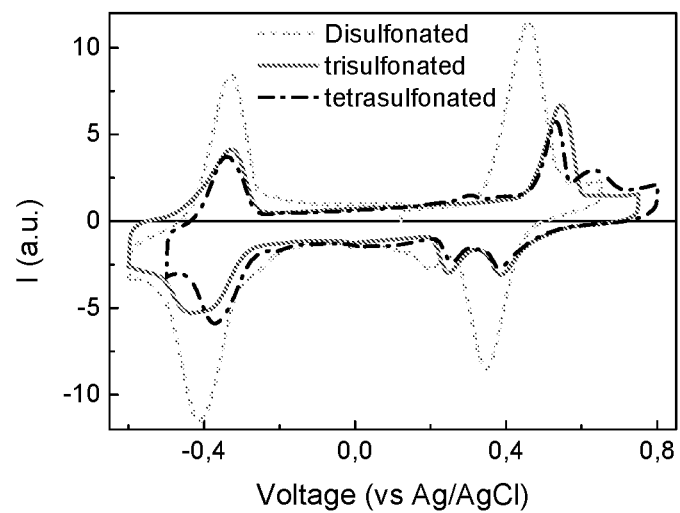
FIG. 4. Three-electrode cell measurements of Indigo derivatives. Cyclic Voltammograms of Indigo derivatives in aqueous solutions at different pH wherein: (a) is the first cycle of Indigo and Indigo Carmine in aqueous buffered solution of BR at pH 7; (b) is the protonated Indigo Carmine in BR pH 3 and 9 (cycles 1 and 10); (c) is the protonated Indigo Carmine in deionized water pH 6.5 and BR pH 7; (d) is the Indigo-TKEN (up) and Indigo TKMP (bottom) in BR solution at pH 7 (d); and (e) is a comparative between Indigo Carmine and tri- and tetra-sulfonated Indigo. Pt was used as counter electrode and Ag/AgCl as reference electrode; Scan rate=200 mV s$^{-1}$.

As depicted in FIG. 4(e), trisulfonate and tetrasulfonate indigo derivatives did not show such a symmetric high voltage peaks as the disulfonated (Indigo Carmine) derivative with the reduction peak being splitted into two peaks.

Anthracene Derivatives

FIG. 5 shows the electrochemical activity of the bisquinones (Quinizarin and Alizarin derivatives) in an aqueous solution of 0.1 M $HClO_4$. Although both exhibited high charge transfer reversibility the relative peak intensity for parent Quinizarin (non-sulphonated) (FIG. 5a, continuous line) was approximately twice than for the less symmetric isoelectronic isomer Alizarin (FIG. 5b, continuous line). Sulphonation of both quinones (FIGS. 5a and 5b, discontinuous lines) caused a decrease of intensity and shifted the redox potential at which the two electron-proton reactions happened which confirms that sulphonation of quinizarin was successful. Shifts of ~100 mV and ~50 mV in quinizarin and alizarin respectively for the lower oxidation state but only ~15 mV and ~35 mV respectively for the upper one are observed in comparison to the parent molecule. The presence of electron attracting groups increases the reduction potential corresponding to both redox stages (the molecule becomes more oxidizing) like shown for the Indigo Carmine molecule. The drop of intensity of the peaks for the sulphonated bis-quinones might be related to the changes of intramolecular hydrogen bonding that the presence of the sulphonate group in alpha of the hydroxyl group effects. Intramolecular hydrogen bonding plays a critical role in the limitation of the electron-proton coupling transfer and reflects the importance of position of the two-hydroxyl groups in the molecule inducing a competition between the remaining hydrogen atoms and the incoming proton for the interaction with the carbonyl oxygen.

Figure 5B:
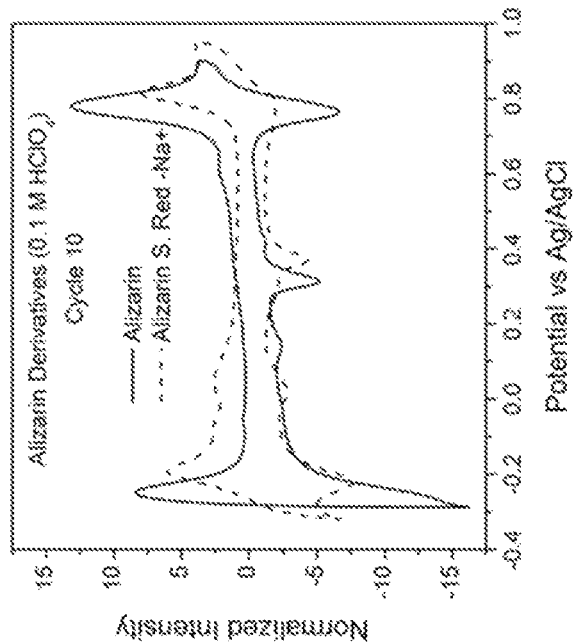
FIG. 5. Electrochemical characterization of the Bisquinones derivatives by using a three-electrode cell configuration. Cyclic Voltammograms in an aqueous solution containing 0.1 M $HClO_4$ wherein: (a) refers to Quinizarin and Quinizarin-$SO_3$Na; (b) refers to Alizarin and Alizarin S. Red; (c) refers to protonated and exchanged Quinizarin; (d) refers to Alizarin S. Red protonated and exchanged with tetra-hydroxyl substituted ammonium and phosphonium cations; and (e) refers to a comparative between Alizarine and Quinizarin with respect to anthraquinone-2-sulfonic acid sodium salt and anthrarufine 1,5-dihydroxyanthraquinone. (Pt was used as counter electrode and Ag/AgCl as reference electrode; Scan rate=200 mV s$^{-1}$).
Figure 5A:
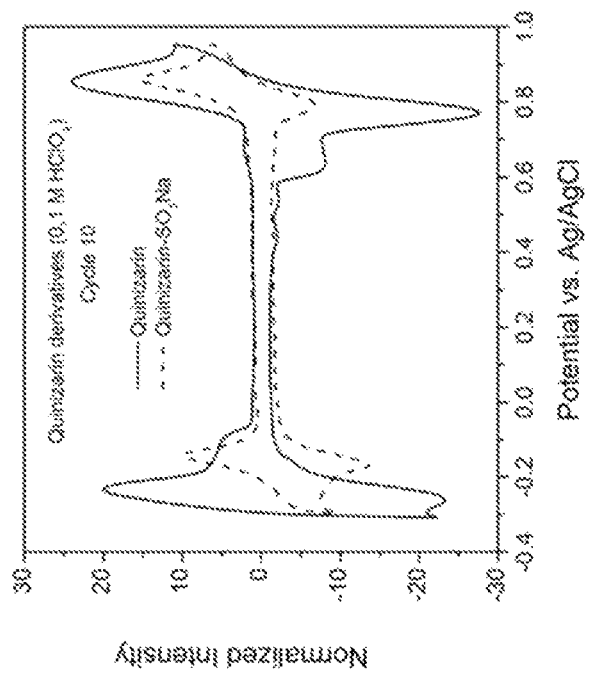
Figure 5C:
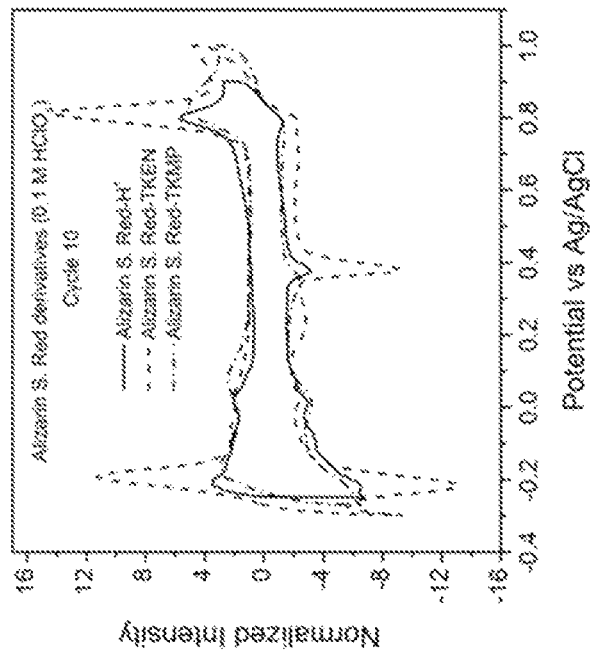
Figure 5D:
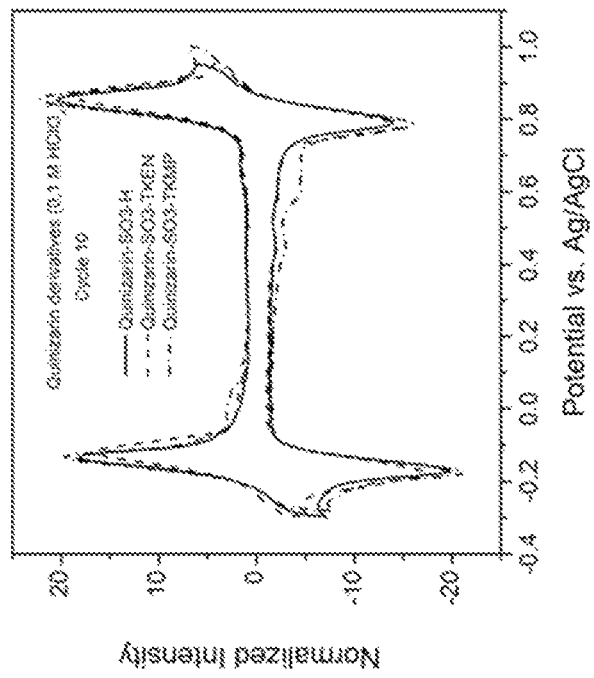

The electrochemistry was kept almost intact in all sulphonated quinizarin salts regardless of the cation counterbalancing the charge (FIG. 5c) while there are major changes in the intensity of the redox processes when changing the cation on the sulphonated Alizarines (FIG. 5d). The intermediate redox peaks observed in Alizarin compounds (FIG. 5d) are probably due to the association between two or more of the flat molecules (n-type interaction and donor/acceptor) of the quinhydrone type and the sharp cathodic peak at ~0.4 V due to quinone trapping in the oxidized state.

Less pronounced redox processes are observed in the most soluble samples, 1.6 M for Alizarin S. Red-$H^+$ and Alizarin S. Red-TKMP when compared with the very well defined redox processes of less soluble quinizarine derivatives (less 0.4 M). Given the fact that the electrochemical measurements were made in a microcavity electrode with powdered samples mixed with conducting carbon in the solid state, the peak sharpness might be affected by the looser electron transfer in the highly soluble samples. Therefore in such conditions a 1 V flow cell could function with two 1.6 M solutions of Alizarin S. Red-$H^+$ or Alizarin S. Red-TKEN. Because the solubility is similar to that of Vanadium based-Redox Batteries (VRB), the voltage is smaller 1 V vs 1.4 V of VRB but the number of electrons per active specie is double, 1.4 times more energy density can be stored in this cell, which although it also operates in acidic media, pH 1, (despite being equally soluble in BR pH 7, it is not electrochemically active) it can be a less expensive option. Moreover the reduced voltage window avoids electrolyte decomposition in the charged state.

Also for comparative purposes, the cyclic voltammograms of anthraquinone derivatives where no hydroxyl groups are present or having hydroxyl groups in different positions than those of the present invention were also tested. The particular compounds were:

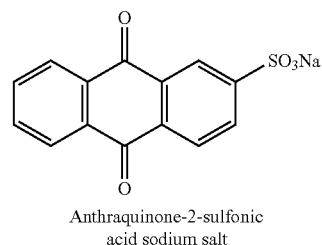

Anthraquinone-2-sulfonic acid sodium salt

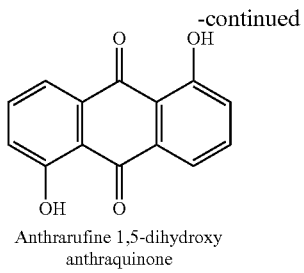

Anthrarufine 1,5-dihydroxy anthraquinone

Figure 5E:
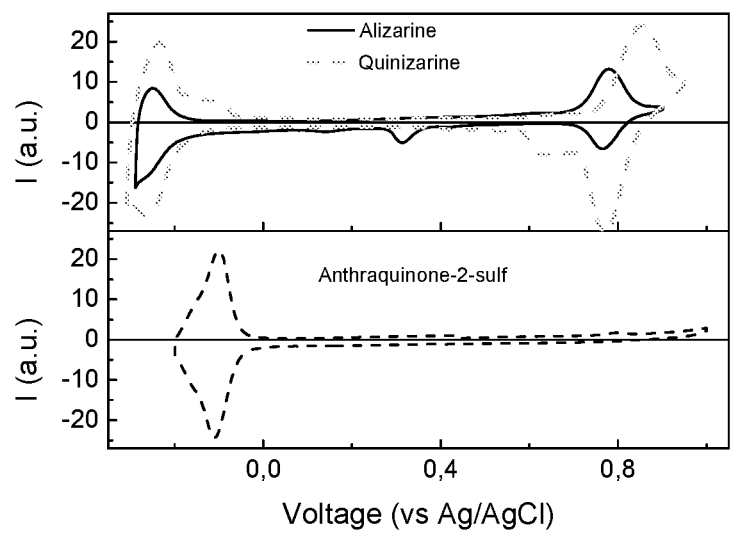
Figure 5E:
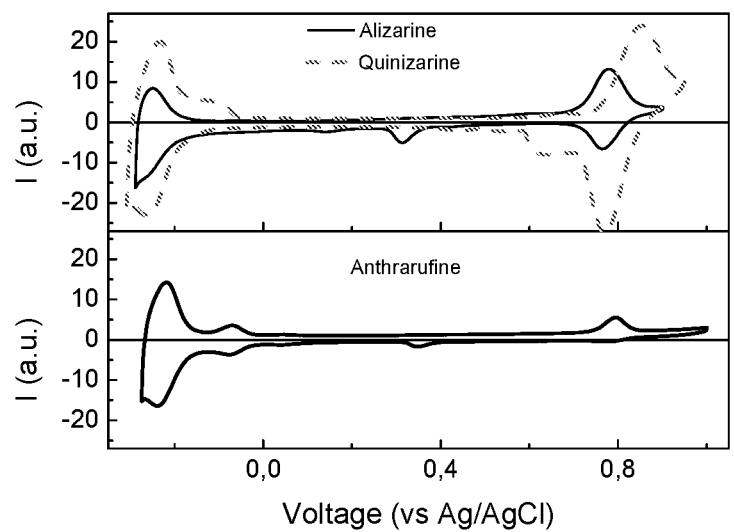

As depicted in FIG. 5(e), said comparative anthraquinone derivatives did not yield two symmetric redox peaks in contrast to the derivatives used in the present invention.

Example 10. Differential Scanning Calorimetry (DSC) Analysis

Figure 6:
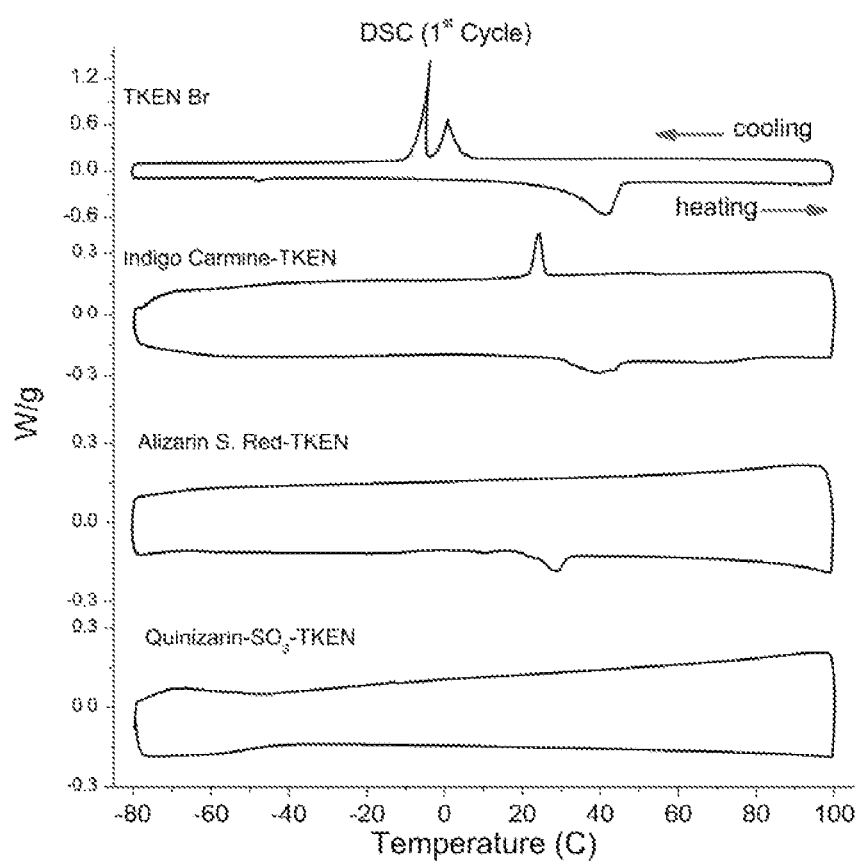
FIG. 6. Differential Scanning Calorimetry (DSC) for TKEN derived salts. DSC traces corresponding to the first heating-cooling cycle for (a) TKEN-Br, (b) Indigo Carmine-TKEN, (c) Alizarin S. Red-TKEN (d) and Quinizarin-$SO_3$-TKEN salt derivatives.

FIG. 6 shows the differential scanning calorimetry (DSC) analysis for some TKEN containing salts. Interestingly, some of them like Indigo Carmine-TKEN (second curve starting from the top) and Alizarin S. Red-TKEN (third curve starting from the top) melt near room temperature (RT). The use of redox-active ionic liquids could boost the energy of the system if only the redox active analyte is used without the need of solvents.

The invention claimed is:

1. A redox organic electrolyte comprising a compound selected from:

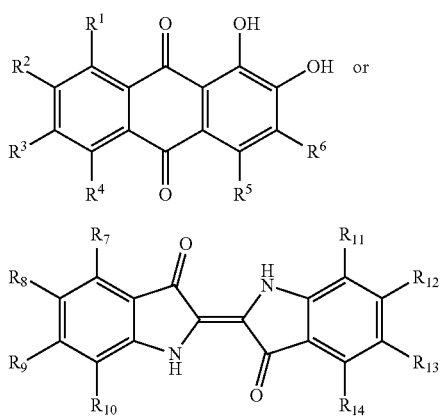

wherein in the compound of formula (i):
$R_1$-$R_6$ are independently selected from the group consisting of hydrogen; $C_1$-$C_6$ alkyl, optionally substituted with at least one halogen and/or optionally having at least one of O- and N-atom in the alkyl chain; $CO_2H$; OH; $NR^{15}R^{16}$ and $SO_3^-M^+$;
provided that at least one of $R_1$-$R_6$ is $SO_3^-M^+$ and
wherein $M^+$ is a cation selected from the group consisting of ammonium cation, phosphonium cation, imidazolium cation and mixtures thereof;
wherein in the compound of formula (iii):
$R_7$-$R_{14}$ are independently selected from the group consisting of hydrogen; $C_1$-$C_6$ alkyl, optionally substituted with at least one halogen and/or optionally having at least one of O- and N-atom in the alkyl chain; $CO_2H$; OH; $NR^{15}R^{16}$ and $SO_3^-M^+$;
provided that two of $R_7$-$R_{14}$ are $SO_2^-M^+$ and wherein:
$R^{15}$ and $R^{16}$ are independently selected from the group consisting of H and $C_1$-$C_6$ alkyl; and
$M^+$ is a cation selected from the group consisting of ammonium cation, phosphonium cation, imidazolium cation and mixtures thereof.

2. The redox organic electrolyte according to claim 1, wherein in the compound of formula (i), $R^1$-$R^5$ are all H, and $R^6$ is $SO_3^-M^+$, wherein $M^+$ is selected from the group consisting of $[N(CH_2CH_2OH)_4]^+$, $[CH_2N(CH_2CH_2OH)_3]^+$, $[(CH_3)_2N(CH_2CH_2OH)_2]^+$ and $[P(CH_2OH)_4]^+$.

3. The redox organic electrolyte according to claim 1, wherein in the compound of formula (iii), $R^7$-$R^8$, $R^{10}$-$R^{11}$ and $R^{13}$-$R^{14}$ are all H, and $R^9$ and $R^{12}$ are $SO_3^-M^+$, wherein $M^+$ is independently selected from the group consisting of $[N(CH_2CH_2OH)_4]^+$, $[CH_2N(CH_2CH_2OH)_2]^+$, $[(CH_3)_2N(CH_2CH_2OH)_2]^+$ and $[P(CH_2OH)_4]^+$.

4. The redox organic electrolyte according to claim 1, further comprising a compound selected from the group consisting of:

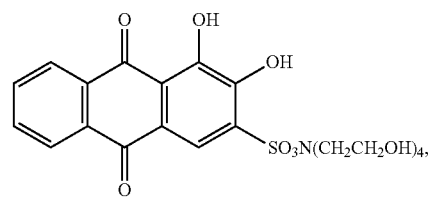

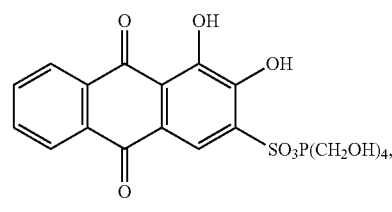

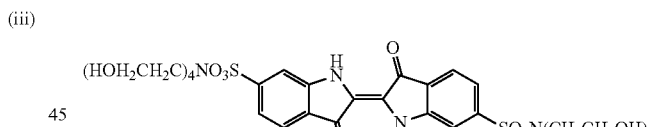

and

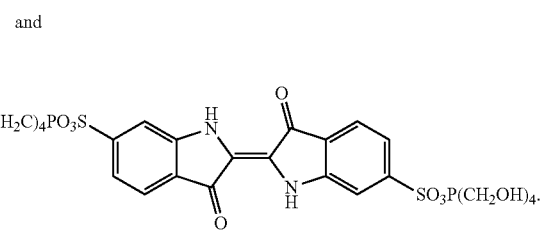

5. The redox organic electrolyte according to claim 1 wherein the electrode is in a liquid phase forming an electrolyte solution.

6. The redox organic electrolyte according to claim 5, wherein the redox organic electrolyte solution further comprises a solvent.

7. The redox organic electrolyte according to claim 6, wherein the solvent is water.

8. A compound selected from:

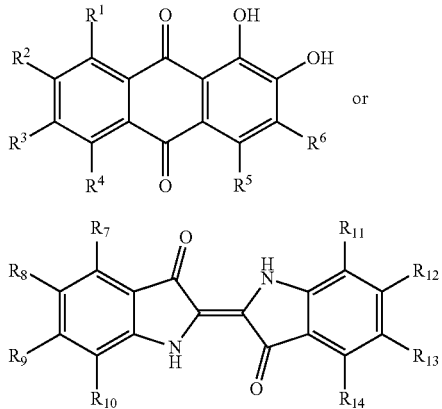

wherein $R_1$-$R_6$ are independently selected from a group consisting of a hydrogen; $C_1$-$C_6$ alkyl, optionally substituted with at least one halogen and/or optionally having at least one of O— and N— atom in the alkyl chain; $CO_2H$; OH; $NR^{15}R^{16}$ and $SO_3^-M^+$;

provided that at least one of $R_1$-$R_6$ is $SO_3^-M^+$;

$R_7$-$R_{14}$ are independently selected from a group consisting of a hydrogen; $C_1$-$C_6$ alkyl, optionally substituted with at least one halogen and/or optionally having at least one of O- and N-atom in the alkyl chain; $CO_2H$; OH; $NR^{15}R^{16}$ and $SO_3^-M^+$;

provided that two of $R_7$-$R_{14}$ are $SO_3^-M^+$;

and wherein:

$R^{15}$ and $R^{16}$ are independently selected from H and $C_1$-$C_6$ alkyl; and $M^+$ is a cation selected from a group consisting of an ammonium cation, a phosphonium cation, an imidazolium cation and mixtures thereof.

9. The compound as defined in claim 8, wherein $M^+$ is selected from a group consisting of $[N(CH_2CH_2OH)_4]^+$, $[CH_3N(CH_2CH_2OH)_3]^{3o}$, $[(CH_3)_2N(CH_2CH_2OH)_2]^+$ and $[P(CH_2OH)_4]^+$.

10. A redox-flow battery comprising a cathode cell comprising a cathode and a catholyte; an anode cell comprising an anode and an anolyte; and an ion exchange membrane disposed between the cathode cell and the anode cell, wherein one of the catholyte or the anolyte comprises the redox organic electrolyte as defined in claim 1.

11. The redox-flow battery according to claim 10, further comprising a catholyte tank and an anolyte tank wherein the catholyte tank and the anolyte tank is each respectively in fluid communication with the cathode cell and the anode cell.

12. A redox-flow battery comprising a cathode cell comprising a cathode and a catholyte; an anode cell comprising an anode and an anolyte; and optionally an ion exchange membrane disposed between the cathode cell and the anode cell, wherein both the catholyte and the anolyte comprise the same redox organic electrolyte as defined in claim 1.

13. A redox-flow supercapacitor, an electrochromic display or photochemical cell comprising the redox organic electrolyte as defined in claim 1.

* * * * *